(12) United States Patent
Bellan et al.

(10) Patent No.: US 9,242,027 B2
(45) Date of Patent: Jan. 26, 2016

(54) FABRICATION OF A VASCULAR SYSTEM USING SACRIFICIAL STRUCTURES

(75) Inventors: Leon M. Bellan, Somerville, MA (US); Harold Craighead, Ithaca, NY (US); Jason A. Spector, New York, NY (US)

(73) Assignee: Cornell University, Ithaca, NY (US)

( * ) Notice: Subject to any disclaimer, the term of this patent is extended or adjusted under 35 U.S.C. 154(b) by 728 days.

(21) Appl. No.: 13/054,450

(22) PCT Filed: Jul. 16, 2009

(86) PCT No.: PCT/US2009/050856
§ 371 (c)(1),
(2), (4) Date: Apr. 15, 2011

(87) PCT Pub. No.: WO2010/009320
PCT Pub. Date: Jan. 21, 2010

(65) Prior Publication Data
US 2011/0270412 A1    Nov. 3, 2011

Related U.S. Application Data

(60) Provisional application No. 61/081,898, filed on Jul. 18, 2008.

(51) Int. Cl.
| | | |
|---|---|---|
| A61F 2/02 | (2006.01) | |
| B29C 69/02 | (2006.01) | |
| B29C 47/06 | (2006.01) | |
| A61M 31/00 | (2006.01) | |
| A61L 27/38 | (2006.01) | |
| A61L 27/54 | (2006.01) | |
| A61L 27/56 | (2006.01) | |
| A61L 27/58 | (2006.01) | |

(52) U.S. Cl.
CPC ............ *A61L 27/3808* (2013.01); *A61L 27/54* (2013.01); *A61L 27/56* (2013.01); *A61L 27/58* (2013.01); *A61L 2300/412* (2013.01); *A61L 2300/414* (2013.01); *A61L 2300/426* (2013.01); *A61L 2300/602* (2013.01)

(58) Field of Classification Search
None
See application file for complete search history.

(56) References Cited

U.S. PATENT DOCUMENTS

| | | | |
|---|---|---|---|
| 5,759,830 A | 6/1998 | Vacanti et al. | |
| 6,103,255 A | 8/2000 | Levene et al. | |
| 6,451,059 B1 | 9/2002 | Janas et al. | |
| 6,673,285 B2 | 1/2004 | Ma | |
| 7,108,914 B2 | 9/2006 | Skipor et al. | |
| 7,371,400 B2 | 5/2008 | Borenstein et al. | |
| 7,387,813 B2 | 6/2008 | Kumar et al. | |
| 2002/0182241 A1 | 12/2002 | Borenstein et al. | |
| 2003/0003575 A1 | 1/2003 | Vacanti et al. | |
| 2004/0203146 A1 | 10/2004 | Gazit et al. | |
| 2004/0226620 A1 | 11/2004 | Therriault et al. | |
| 2006/0018838 A1* | 1/2006 | George et al. | 424/44 |
| 2006/0125144 A1* | 6/2006 | Weber et al. | 264/309 |
| 2006/0127437 A1 | 6/2006 | Kennedy et al. | |
| 2006/0129179 A1* | 6/2006 | Weber et al. | 606/194 |
| 2006/0136182 A1 | 6/2006 | Vacanti et al. | |
| 2006/0195179 A1 | 8/2006 | Sun et al. | |

FOREIGN PATENT DOCUMENTS

| | | |
|---|---|---|
| DE | 103 13 291 A1 | 10/2004 |
| WO | 2009/048548 A1 | 4/2009 |

OTHER PUBLICATIONS

Bellan et al., "Fabrication of an Artificial 3-Dimensional Vascular Network Using Sacrificial Sugar Structures," Soft Matter 5(7):1354-57 (2009).
Borenstein et al., "Microfabrication of Three-Dimensional Engineered Scaffolds," Tissue Eng. 13(8):1837-44 (2007).
PCT/US2009/050856, International Preliminary Report on Patentability (Jan. 18, 2011).
Akita et al., "Capillary Vessel Network Integration by Inserting a Vascular Pedicle Enhances Bone Formation in Tissue-Engineered Bone Using Interconnected Porous Hydroxyapatite Ceramics," Tissue Eng. 10(5-6):789-795 (2004).
Ashammakhi et al., "Biodegradable Nanomats Produced by Electrospinning: Expanding Multifunctionality and Potential for Tissue Engineering," J. Nanosci. Nanotechnol. 7(3):862-882 (2007).
Kim et al., "Fabrication of a New Tubular Fibrous PLCL Scaffold for Vascular Tissue Engineering," J. Biomater. Sci. Polym. Ed. 17(12):1359-74 (2006).

(Continued)

*Primary Examiner* — Robert A Wax
*Assistant Examiner* — Randeep Singh
(74) *Attorney, Agent, or Firm* — LeClairRyan, a Professional Corporation

(57) ABSTRACT

The first aspect of the present invention is directed to a method of producing a vascular network preform (VNP). This method involves forming a network of elongate fibers and at least one elongate structure from a sacrificial material. The diameter of the elongate structure is greater than that of the elongate fibers. The network of elongate fibers is placed in contact with at least one elongate structure either following or during forming the network of elongate fibers or forming the at least one elongate structure. A matrix is applied around the network of elongate fibers, in contact with the at least one elongate structure. The network of elongate fibers and elongate structure, within the matrix is sacrificed to form a preform. The resulting preform contains a vascular network of fine diameter tubes in contact with at least one elongate passage having a diameter greater than that of the fine diameter tubes. The resulting solid preform and methods of using it are also disclosed.

47 Claims, 14 Drawing Sheets

(56) References Cited

OTHER PUBLICATIONS

Bianchi et al., "Microfabrication of Fractal Polymeric Structures for Capillary Morphogenesis: Applications in Therapeutic Angiogenesis and in the Engineering of Vascularized Tissue," J. Biomed. Mater. Res. Part B Appl. Biomater. 81B:462-468 (2007.
Black et al., "In Vitro Reconstruction of a Human Capillary-Like Network in a Tissue-Engineered Skin Equivalent," FASEB J. 12(13):1331-1340 (1998).
Borenstein et al., "Living Three-Dimensional Micro Fabricated Constructs for the Replacement of Vital Organ Function," Transducers '03. Digest of Technical Papers/12th International Conference on Solid-State Sensors, Actuators and Microsystems 2:1754-1757 (2003).
Bursac et al., "Novel Anisotropic Engineered Cardiac Tissues: Studies of Electrical Propagation," Biochem. Biophys. Res. Commun. 361:847-853 (2007).
Cooke et al., "Use of Stereolithography to Manufacture Critical-Sized 3D Biodegradable Scaffolds for Bone Ingrowth," J. Biomed. Mater. Res. 64B:65-69 (2003).
Golden and Tien, "Fabrication of Microfluidic Hydrogels Using Molded Gelatin as a Sacrificial Element," Lab Chip 7:720-725 (2007).
Pham et al., "Electrospinning of Polymeric Nanofibers for Tissue Engineering Applications: A Review," Tissue Engineering 12(5):1197-211 (2006).
Ikeuchi & Ikuta, "Artificial Capillary Network Chip for in Vitro 3D Tissue Culture," Transducers '07 & Eurosensors XXI. 14th International Conference on Solid-State Sensors, Actuators and Microsystems pp. 1337-1340 (2007).
Iyer et al., "Synthetic Oxygen Carriers in Cardiac Tissue Engineering," Artif. Cells, Blood Substit. Immobil. Biotechnol. 35(1):135-148 (2007).
Kannan et al., "The Roles of Tissue Engineering and Vascularisation in the Development of Micro-Vascular Networks: A Review," Biomaterials 26(14):1857-1875 (2005).
Ko et al., "Engineering Thick Tissues—the Vascularisation Problem," Eur. Cell Mater. 14:1-19; Discussion 18-19 (2007).
Li et al., "Biomimetic Nerve Scaffolds With Aligned Intraluminal Microchannels: A 'Sweet' Approach to Tissue Engineering," Langmuir 25:1813-1817 (2009).
Liu et al., "Construction of a Tissue Engineering Skin Containing Capillary-Like Networks," Zhongguo Xiu Fu Chong Jian Wai Ke Za Zhi 18(6):502-504 (2004) (Abstract only).
Lokmic & Mitchell, "Engineering the Microcirculation," Tissue Eng. Part B. Rev. 14(1):87-103 (2008) (Abstract only).
Ma et al., "Potential of Nanofiber Matrix as Tissue-Engineering Scaffolds," Tissue Eng. 11(1-2):101-109 (2005) (Abstract only).
Mironov et al., "Organ Printing: Computer-Aided Jet-Based 3D Tissue Engineering," Trends Biotechnol. 21:157-161 (2003).
Nazhat et al., "Controlled Microchanneling in Dense Collagen Scaffolds by Soluble Phosphate Glass Fibers," Biomacromol. 8(2):543-551 (2007).
Neumann et al., "Tissue Engineering of Perfused Microvessels," Microvasc. Res. 66(1):59-67 (2003) (Abstract only).
Okano & Matsuda, "Muscular Tissue Engineering: Capillary-Incorporated Hybrid Muscular Tissues in Vivo Tissue Culture," Cell Transplant. 7(5):435-442 (1998).
Radisic et al., "Biomimetic Approach to Cardiac Tissue Engineering: Oxygen Carriers and Channeled Scaffolds," Tissue Eng. 12(8):2077-2091 (2006) (Abstract only).
Ryu et al., "The Construction of Three-Dimensional Micro-Fluidic Scaffolds of Biodegradable Polymers by Solvent Vapor Based Bonding of Micro-Molded Layers," Biomater. 28(6):1174-1184 (2007).
Sherwood et al., "A Three-Dimensional Osteochondral Composite Scaffold for Articular Cartilage Repair," Biomater. 23:4739-4751 (2002).
Smith et al., "Three-Dimensional BioAssembly Tool for Generating Viable Tissue-Engineered Constructs," Tissue Eng. 10:1566-1576 (2004).
Smith et al., "Characterizing Environmental Factors That Impact the Viability of Tissue-Engineered Constructs Fabricated by a Direct-Write BioAssembly Tool," Tissue Eng. 13(2):373-383 (2007).
Sodian et al., "Early in Vivo Experience With Tissue-Engineered Trileaflet Heart Valves," Circulation 102:III-22-III-29 (2000).
Schultheiss et al., "Biological Vascularized Matrix for Bladder Tissue Engineering: Matrix Preparation, Reseeding Technique and Short-Term Implantation in a Porcine Model," J. Urol. 173:276-280 (2005).
Takei et al., "Fabrication of Artificial Endothelialized Tubes With Predetermined Three-Dimensional Configuration From Flexible Cell-Enclosing Alginate Fibers," Biotechnol. Prog. 23(1):182-186 (2007).
Satake et al., "Tissue Engineering Approach to Reconstruct the Capillary Network at Subcutaneous and Intermuscular Sites for Bioartificial Pancreas Transplantation," Pancreas 21(4): 475 (2000) (Meeting).
Auger et al., "Formation of Human Capillary-like Network in a Tissue-engineered Skin Equivalent", FASEB J. 13(4): A527 (1999) (Meeting Abstract).
Balamurugan et al., "Bioartificial Pancreas Transplantation at Prevascularized Intermuscular Space: Effect of Angiogenesis Induction on Islet Survival," Pancreas 26(3):279-285 (2003.
International Search Report and Written Opinion for PCT/US2009/050856 (Sep. 8, 2009).
Ben-Ze'ev et al., "Cell-Cell and Cell-Matrix Interactions Differentially Regulate the Expression of Hepatic and Cytoskeletal Genes in Primary Cultures of Rat Hepatocytes," Proc. Natl. Acad. Sci. U.S.A. 85:2161-2165 (1988).
Edelman et al., "Cell Adhesion Molecules: Implications for a Molecular Histology," Annu. Rev. Biochem. 60, 155-190 (1991).
Folkman et al., "Self-Regulation of Growth in Three Dimensions," J. Exp. Med. 138:745-753 (1973).
Geiger et al., "Cadherins," Annu. Rev. Cell Biol. 8:307-332 (1992).
Hoerstrup et al., "Functional Living Trileaflet Heart Valves Grown in Vitro," Circulation 102(suppl III):III-44-III-49 (2000).
Juliano, "Signal Transduction by Cell Adhesion Receptors and the Cytoskeleton: Functions of Integrins, Cadherins, Selectins, and Immunoglobulin-Superfamily members," Annu. Rev. Pharmacol. Toxicol. 42:283-323 (2002).
Larue et al., "A Role for Cadherins in Tissue Formation," Development 122:3185-3194 (1996).
Madri et al., "Capillary Endothelial Cell Cultures: Phenotypic Modulation by Matrix Components," J. Cell Biol. 97:153-165 (1983).
McDevitt et al., "In Vitro Generation of Differentiated Cardiac Myofibers on Micropatterned Laminin Surfaces," J. Biomed. Mater. Res. 60:472-479 (2002).
Miyajima et al., "Risk Factors for Major Limb Amputations in Diabetic Foot Gangrene Patients," Diabetes Res. Clin. Pract. 71:272-279 (2006).
Shibuya et al., "Localization of N-Cadherin in the Normal and Regenerating Nerve Fibers of the Chicken Peripheral Nervous System," Neuroscience 67(1):253-261 (1995).
Takeichi, "Morphogenetic Roles of Classic Cadherins," Curr. Opin. Cell Biol. 7:619-627 (1995).
Wagner et al., "The Isolation and Culture of Capillary Endothelium from Epididymal Fat," Microvasc. Res. 10:286-297 (1975).
Wessells et al., "Endothelial Cell Transplantation into the Corpus Cavernosum: Moving Towards Cell-Based Gene Therapy," J. Urol. 162:2162-2164 (1999).
Yeaman et al., "New Perspectives on Mechanisms Involved in Generating Epithelial Cell Polarity," Physiological Rev. 79(1)73-98 (1999).
Zahir et al., "Death in the Third Dimension: Apoptosis Regulation and Tissue Architecture," Curr. Opin. Genet. Dev. 14:71-80 (2004).

* cited by examiner

US 9,242,027 B2

FABRICATION OF A VASCULAR SYSTEM USING SACRIFICIAL STRUCTURES

This application claims the benefit of U.S. Provisional Patent Application Ser. No. 61/081,898, filed Jul. 18, 2008.

This invention was made with government support under grant numbers HRD-0630456, ECS-9876771, and DMR-0520404 by the National Science Foundation. The government has certain rights in this invention.

FIELD OF THE INVENTION

The present invention is directed to the fabrication of vascular systems using sacrificial structures.

BACKGROUND OF THE INVENTION

Acute and chronic wounds are a significant burden to the healthcare system affecting millions of patients nationally and resulting in billions of dollars of outlays. Every year several million people suffer irreversible damage or loss of one or more tissue or organ systems, resulting in disfigurement, loss of function, physiologic derangement, and death.

A major leap forward in reconstructive surgery occurred in the 1960's and continued through the following decade with the discovery of "axial flaps". Using detailed anatomic analysis, reconstructive surgeons determined that large portions of composite tissues (e.g., skin and muscle, skin and bone, skin and fascia etc.), designated "flaps" could be reliably moved from one portion of the body (donor) to an adjacent area (recipient). The development of microsurgery was the next major breakthrough. Now with the aid of an operating microscope, surgeons could reliably suture arteries and veins as small as 1 mm in diameter with patency rates over 95%. Whereas previously donor tissues could only be moved as far as their vascular "leash" would allow, microsurgical techniques have enabled reconstructive surgeons to move tissues from and to anywhere in the body, as long as recipient vessels (to which the flap artery and vein could be sewn) are found.

Despite the numerous benefits associated with tissue transfer, there are certainly drawbacks associated with these complex reconstructive procedures. Harvesting the donor tissue is a complicated process and the resultant donor sites are often painful and carry substantial morbidity, especially in the diabetic population. Patients who are elderly or carry other co-morbidities such as cardiopulmonary or renal disease are especially at risk for significant peri-operative complications because of the long anesthesia times, notable blood loss, and large fluid shifts.

If suitable replacement tissue could be fabricated with its own microvascular network and vascular leash (for attachment to host vasculature), it will be possible to create "off the shelf constructs" which could then be anastomosed to the required area of deficiency in a surgically reliable, safe, and expeditious manner.

Although the field of tissue engineering holds great promise for the fabrication of functional implantable materials (Langer et al., *Science* 260:920-926 (1993)), the ability to design artificial tissue constructs that have their own inherent vascular network remains a critical limiting step (Saltzman et al., *Nat Rev Drug Disc* 1:177-186 (2002)). Without such a network, any implanted engineered tissue must rely upon host vessel ingrowth for vascularization. However, because of the slow pace of vascular ingrowth, tissue engineers are constrained to designing constructs no thicker than a few millimeters, the limit of diffusion of nutrients from a vascular to a non-vascular area (Androjna et al., *Tissue Engineering Part A* 14:559-569 (2008)). Diffusion of nutrients is highly limited and, therefore, restricts the size and thickness of artificial tissue implants. In vivo, most cells cannot survive more than a few hundred micrometers away from the nearest capillary (Frerich et al., *Int J Oral Maxill of* 30:414-420 (2001); Okano et al., *Cell transplant* 7:435-442 (1998); Sheridan et al., *J Control Release* 64:91-102 (2000)). Cells distant from a vascular area are prone to ischemic death because of a paucity of oxygen and nutrients required for cellular metabolism.

Moreover, to be clinically useful, a tissue engineered construct must have not only a 3D vascular network, but also the ability to be "spliced" into the host blood supply, allowing for immediate vascularization of the construct and assuring the survival of the cellular constituents within. The creation of such vascularized constructs is currently beyond the capabilities of any contemporary tissue engineering approach. To rectify this problem, several investigators have endeavored to create a de novo vascular network, which could then be seeded with cells (Takei et al., *Biotechnology Progress* 23:182-186 (2007); Kannan et al., *Biomaterials* 26:1857-1875 (2005); Lim et al., *Lab on a Chip* 3:318-323 (2003); and McGuigan et al., *Proc Nat'l Acad Sci* 103:11461-11466 (2006)). Because the construct would be "pre-vascularized", it would theoretically be able to pass oxygen and nutrients into the deeper portions of the structure. However, in this scenario, the vascular network would have to be immediately perfused by the host's blood in order for the deeper portions of the construct to survive. This would only be possible if the micro vascular network coalesced into larger vessels that could be reliably (>1 mm in diameter) anastomosed to the host's blood supply. Unfortunately, despite tremendous advances in the understanding of vasculogenesis and angiogenesis, including the creation of capillary-like networks from cellular constituents, investigators have thus far been unable to achieve the goal of creating a confluent de novo microvascular and macrovascular network. Furthermore, the vascular networks that have been constructed remain microscopic in scale, and have not yet been integrated into appropriate tissue engineering scaffolds. In short, the organizational process underlying the development of tissues and organs thus far remains too complex to engineer from "the ground up."

Numerous investigators have attempted to engineer various constructs by placing different cell types on a variety of (3-D) matrices. Current therapeutic strategies rely upon implantation of these tissue-engineered constructs into the host where they will be re-vascularized by host vessel ingrowth. Unfortunately, this is a highly fallible approach since constructs containing cells further than several hundred microns from the surface (the limits of diffusion) are prone to ischemic cell death because of a paucity of oxygen and nutrients required for cellular metabolism. This technological hurdle has significantly stunted the development of tissue engineered products that may be widely applied in the clinical arena. As an example, two of the most "successful" tissue engineered products, Integra™ and Alloderm™, developed primarily as skin substitutes, are both thin (<2 mm thick), acellular and require vascularization from the host in order to "survive". Because of their initial avascularity, both of these constructs are prone to infection and can only be placed in healthy, well vascularized wound beds.

An alternative and much more promising strategy for tissue engineering vascularized constructs would not rely on the assemblage of a (large) construct starting from masses of individual cells. Instead, the ideal strategy would be to build a construct that already contained a vascular "scaffold", with a microvascular bed that coalesced into a "feeding" macrovascular (>1 mm) leash. Such a construct would be ideal as it could be anastomosed to the host blood supply using standard microsurgical techniques, resulting in an immediately perfused, and thus fully viable construct. A variant of this approach has been pursued in a porcine model where a vascularized bladder-like tissue has been successfully created (Schultheiss et al., *J. Uro.* 173:276-280 (2005)). Their method involved de-cellularizing a segment of porcine intestine, then re-perfusing it with endothelial precursors which then re-endothelialized the intact vascular "scaffold". The constructs were then anastomosed to recipient pigs and demonstrated normal blood flow within the re-endothelialized vessels up to one hour post-implantation.

Although these data demonstrate a successful "proof of concept", the utility of this approach is limited by the need for a donor animal to provide the tissue, which must then be chemically treated to remove all cellular constituents. Furthermore, their constructs could not be custom designed by tissue type or shape, attributes that will likely be required when constructing any "replacement part", other than the flat sheet they utilized as a bladder wall replacement.

In general, the methods used for tissue scaffolds range in complexity from forming porous polymeric structures (Chen et al., *Macromol. Biosci.* 2:67-77 (2002) and Mikos et al., *Electronic Journal of Biotechnology vol.* 3 (2000)) (with random hole sizes and positions) to completely designing the construct structure using 3D printing or microfabrication-based technologies (Mironov et al., *Trends in Biotech* 21:157-161 (2003); Khademhosseini et al., *Biomaterials* 28:5087-5092 (2007); and Cooke et al., *Journal of Biomedical Materials Research Part B—Applied Biomaterials* 64B:65-69 (2003)). Several sacrificial techniques have been used to pattern simple microfluidic networks in scaffolds (Golden et al., *Lab on a Chip* 7:720-725 (2007) and Nazhat et al., *Biomacromolecules* 8:543-551 (2007)). To date, none of these techniques have met the necessary dual criteria of providing physiologic flow through 3D microchannel networks with a capability of being surgically integrated into the host macrovasculature.

Thus, comprehensive vascularization of tissue in vitro is a major challenge in fabrication of bioengineered tissue. Creating a proper connection between the engineered tissue and the host vasculature when the tissue is implanted is the next major challenge.

Constructs with three dimensional microfluidic networks have many potential applications, including fluid mixing (Therriault et al., *Nat Mater* 2:265-271 (2003)), providing healing agents in self-healing polymer systems (Toohey et al., *Nat Mater* 6:581-585 (2007)), and artificial vascular networks for engineered tissue (Borenstein et al., *Biomedical Microdevices* 4:167-175 (2002); Shin et al., *Biomedical Microdevices* 6:269-278 (2004); Choi et al., *Nat Mater* 6:908-915 (2007); and Saltzman et al., *Nat Rev Drug Disc* 1:177-186 (2002)). However, three dimensional (3D) fluidic network fabrication is currently time-consuming and difficult, requiring either layer-by-layer assembly of two dimensional (2D) structures formed using standard microfabrication techniques (such as photolithography and imprint lithography) (Luo et al., *Lab on a Chip* 8:1688-1694 (2008); Chiu et al., *Proc. Natl. Acad. Sci. U.S.A.* 98:2961-2966 (2001); McDonald et al., *Acc. Chem. Res.* 35:491-499 (2002)) or 3D printers (Therriault et al., *Nat Mater* 2:265-271 (2003); Toohey et al., *Nat Mater* 6:581-585 (2007); and McDonald et al., *Acc. Chem. Res.* 35:491-499 (2002)).

The present invention is directed to overcoming these and other deficiencies in the art.

SUMMARY OF THE INVENTION

The first aspect of the present invention is directed to a method of producing a vascular network preform (VNP). This method involves forming a network of elongate fibers and at least one elongate structure from a sacrificial material. The diameter of the elongate structure is greater than that of the elongate fibers. The network of elongate fibers is placed in contact with at least one elongate structure either following or during forming the network of elongate fibers or forming the at least one elongate structure. A matrix is applied around the network of elongate fibers, in contact with the at least one elongate structure. The network of elongate fibers and elongate structure within the matrix is sacrificed to form a preform. The resulting preform contains a vascular network of fine diameter tubes in contact with at least one elongate passage having a diameter greater than that of the fine diameter tubes.

Another aspect of the present invention is directed to a solid preform comprising a solid matrix, a vascular network of fine diameter tubes randomly extending in a non-repeating pattern within the solid matrix, and at least one elongate passage having a diameter greater than that of the fine diameter tubes. The at least one elongate passage extending within the solid matrix is in contact with the vascular network of fine diameter tubes.

The present invention also relates to a cell seeded monolith where the solid preform is seeded with cells.

Another aspect of the present invention is directed to a method of treating a patient for a condition requiring vascularization. The method includes providing the above-described cell seeded monolith, selecting a subject with a condition requiring vascularization, and implanting the cell seeded monolith into the selected subject.

The present invention is also directed to a method of forming a self healing material system. This involves providing the above-described solid preform and allowing for the releasing of the healing agent from the vascular network upon injury to or cracking of the solid perform. As a result the injury or crack is filled.

Another aspect of the present invention is directed to transferring heat to a surface or volume. This involves providing the above-described solid preform which is configured such that there is transfer of heat between the solid preform and a fluid present in the vascular network. The fluid is passed through the vascular network so that the solid preform heats or cools the fluid or the fluid heats or cools the solid preform.

The present invention also relates to a method of carrying out a biological reaction. The above cell seeded monolith is provided and fluids are passed through the cell seeded monolith under conditions effective to carry out the biological reaction.

The present invention is directed to the fabrication and use of scalable, rapid, and inexpensive 3-dimensional construct (scaffold) containing micrometer (1-100 µm) size channels connected to millimeter (>500 µm) size inflow and outflow channels. The fabrication technique that has been developed involves the use of sacrificial water-soluble sugar fiber structures (cotton candy and extruded sticks of sugar) over which a construct material (also called matrix) is poured. After the construct material has solidified, the construct is immersed in water to remove the sacrificial structure, leaving a complex 3-dimensional channel network with a random, non-repeating geometry that mimics the vascular networks found in nature. The vascular network preform can be designed to have branching networks which have smaller diameter channels merging into larger diameter channels such that the network mimics native capillaries, arterioles, and venules found in biological tissues. The average density, diameter, and size of the channels in the preform can be readily controlled using this novel engineering approach.

A key advantage of the present invention is the ability to use fibers to make highly branched, larger in scale, two dimensional or three dimensional vascularized constructs. Individual fibers used in the present invention can be fused during the fabrication process to each other and/or to larger diameter tubes. This enables branching and elongation of the channel network, thus enabling fabrication of larger vascularized constructs which are scalable in all three dimensions. Furthermore, the channels can be designed and fabricated such that they are confluent with a feeding "artery" (inlet) and "draining" vein (outlet), both greater than or equal to 500 µm in diameter. These larger vessels can act as the vascular pedicle, or leash, for the tissue implants in which the vascular network preforms (VNPs) can be anastomosed, or connected, to the host vasculature using standard microsurgical techniques.

Techniques relying upon 3D printing for fabricating constructs with vascular networks are available but are prohibitively expensive. The time and expense required to make artificial tissue constructs that have clinically useful sizes or industrially useful amounts would render 3D printing prohibitively expensive. The methods used in this invention are scalable and inexpensive. Also, the shape of the vascularized network preform and the embedded vascular network is highly customizable. For example, the millimeter-sized channels could be placed in a predetermined pattern or shape in order to reproduce the macroscale vascular layout of the tissue to be replaced. The elongate fibers could be combed or exposed to mechanical stretching to align or orient the fibers.

It is the unique capability to scale up the constructs beyond several millimeters in size, the relative ease of fabrication and highly customizable vascularity of the preform which makes the present invention novel.

BRIEF DESCRIPTION OF THE DRAWINGS

FIG. 3A shows the use of heat or ambient humidity to fuse together the fibers that are in contact with each other. FIG. 3B is an enlarged view showing fused fibers after welding.

FIG. 12A shows the image obtained by scanning electron microscopy at different magnifications. FIG. 12B shows the image produced from the maximum pixel values of several slices recorded using multiphoton microscopy (channels visible in this image are in multiple planes). Dilations in the channels are likely due to imperfections in the sacrificial sugar structure or bubbles in the polydimethylsiloxane (PDMS) matrix material that remain during solidification.

In FIG. 14B, individual blood cells are visible.

FIG. 15E shows a vascular network preform made from polycaprolactone (PCL). These demonstrate that the fabrication process is compatible with materials important for structural and biomedical engineering purposes. The constructs are shown filled with water containing red food coloring. FIGS. 15A-C show a top view of an epoxy device as it is filled, demonstrating a noticeable color change. FIG. 15D shows a side view. FIG. 15E shows a cross sectional view of a filled PCL device. As a scale reference, the minimum spacing between the holes in the cloth below the constructs is ~3.4 mm.

DETAILED DESCRIPTION OF THE INVENTION

The first aspect of the present invention is directed to a method of producing a vascular network preform (VNP). This method involves forming a network of elongate fibers and at least one elongate structure from a sacrificial material. The diameter of the elongate structure is greater than that of the elongate fibers. The network of elongate fibers is placed in contact with at least one elongate structure either following or during forming the network of elongate fibers or forming the at least one elongate structure. A matrix is applied around the network of elongate fibers, in contact with the at least one elongate structure. The network of elongate fibers and elongate structure within the matrix is sacrificed to form a preform. The resulting preform contains a vascular network of fine diameter tubes in contact with at least one elongate passage having a diameter greater than that of the fine diameter tubes.

In general, the fabrication method involves forming a network of small sacrificial fibers, to which at least one (preferably two or more) larger sacrificial structure(s) is (are) connected. A matrix, which can be a polymer, is poured or applied over the sacrificial network such that the whole network is embedded in the matrix. The sacrificial network is removed after the matrix has solidified or set such that a perform containing a vascular network of fine diameter tubes in contact with at least one larger passage remains.

Figure 1:
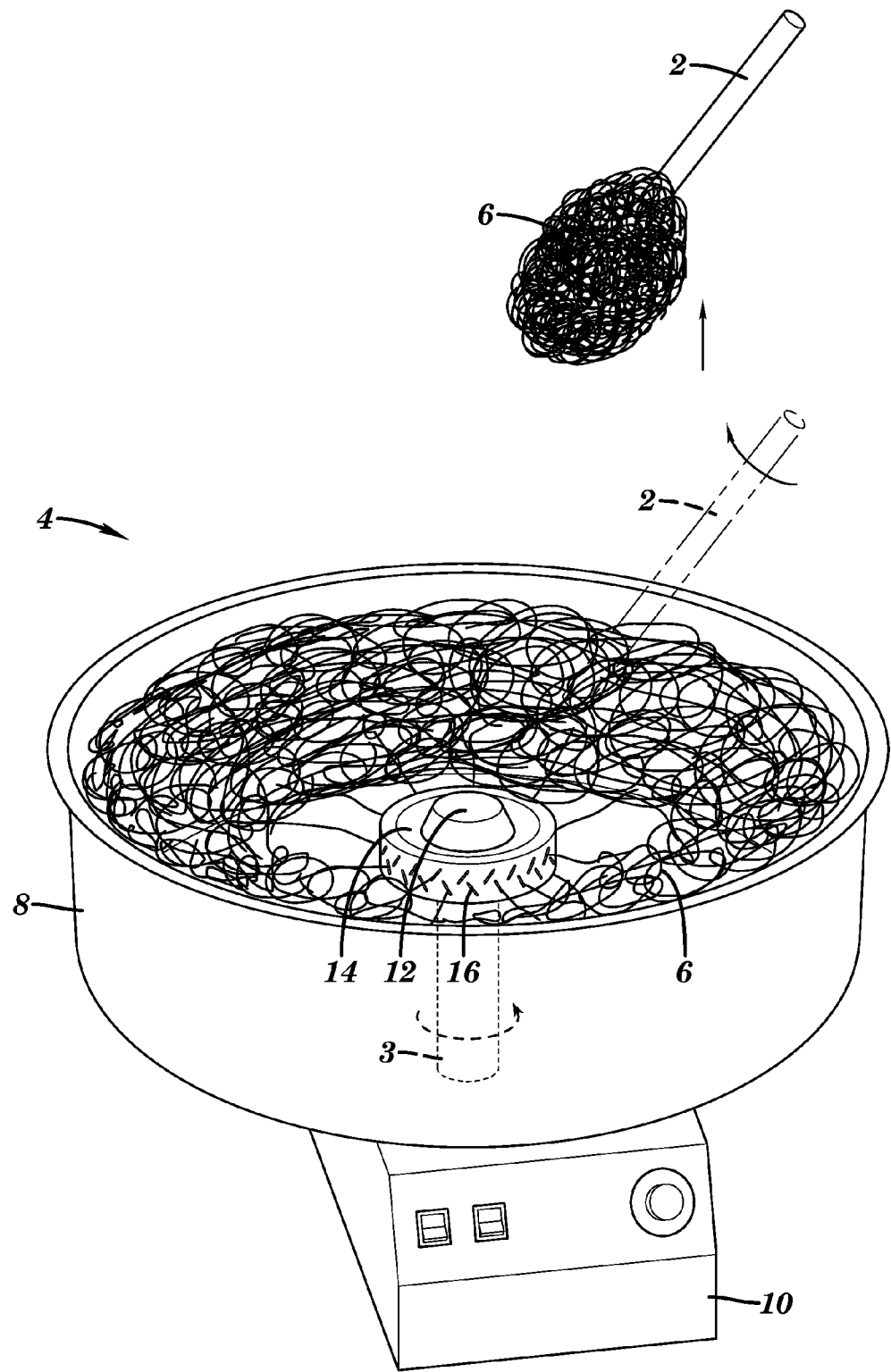
FIG. 1 is the perspective view of the cotton candy machine that is used to make sacrificial elongate fibers from sugar and the stick that can be used to collect the fibers.

The process of fabricating the vascular network preform are illustrated in FIGS. 1-7, as described below. FIG. 1 is a perspective view of a device (e.g., a cotton candy machine) for making fine elongate fibers 6 for the present invention. The components and operation of such devices are well known to those skilled in the art. See U.S. Pat. No. 4,842,502 to Tsumita et al. and U.S. Pat. No. 3,036,532 to Bowe, which are hereby incorporated by reference in their entirety. Device 4 includes housing 10 supporting a tub 8. Housing 10 includes an electric motor, an on-off switch, and several other conventional controls. Tub 8 is used for catching elongate fibers 6 as they are formed. Supported in housing 10, within tub 8, is a head assembly 14. Head assembly 14 is mounted to a shaft 3 coupled to the electric motor in housing 10. Opening 12 is provided in head assembly 14 to permit fiber forming material (e.g., sugar) to be poured into a chamber within head assembly 14 which is provided with a heater to melt sugar. In operation, spinning of spinning head assembly 14 propels fiber forming materials against heater element so that the fiber forming materials melts. As a result, fibers 6 are extruded from slots 16 into tub 8, which is stationary.

The melted fiber forming materials passing through slots 16 forms fibers 6 which are collected in tub 8. Stick 2 is used to pick up fibers 6 from tub 8. The speed of rotation of the head assembly 14 can be changed in order to change properties of the fibers.

Figure 2:
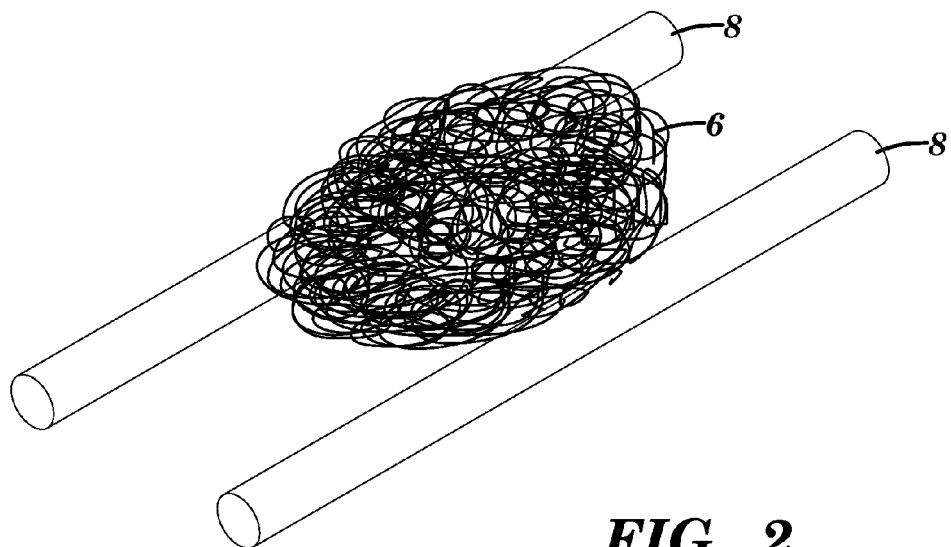
FIG. 2 is a perspective view of an assembly of sacrificial elongate fibers and sacrificial elongate structure, when placed in contact with one another.

Fibers 6 are then placed in contact with elongate structures 8 in a desired configuration, as shown in FIG. 2. This arrangement of fibers 6 and elongate structures 8 serves as a template for the vascular network. Elongate structures 8 can be hollow or solid. Fibers 6 and elongate structures 8 can be made from the same or different materials.

Figure 3A:
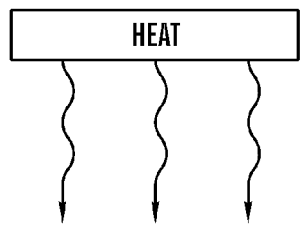
FIGS. 3A-B show the process of welding or connecting of sacrificial fibers to each other and to the sacrificial elongate fibers.
Figure 3B:
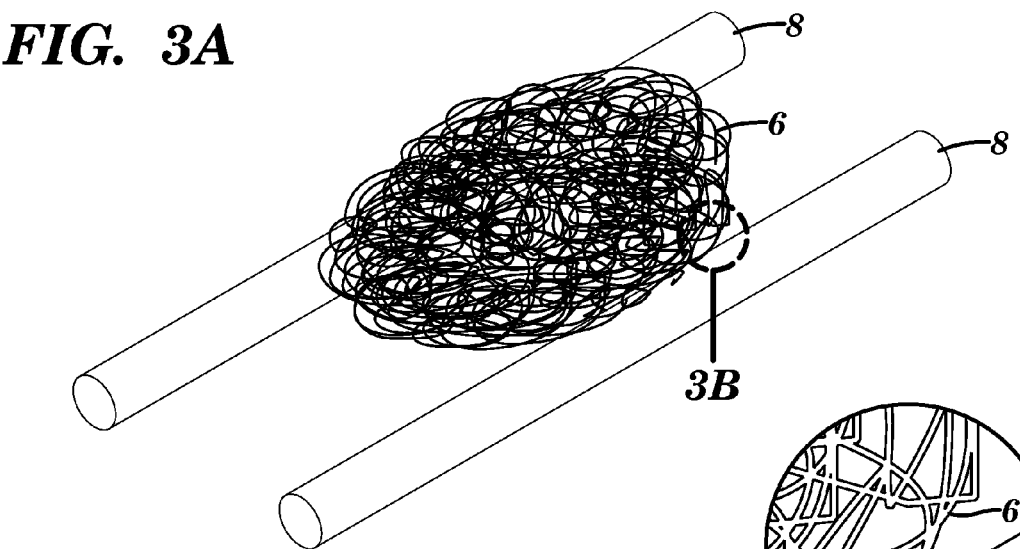

FIG. 3A illustrates the next optional step in the process where fibers 6 are welded or connected to one another and to elongate structures 8 using heat or humidity treatment. This fuses the fibers together to produce branched network of connected fibers, as shown enlarged in FIG. 3B. FIG. 3B also shows the fusion of fibers 6 to elongate structures 8. The amount and duration of this treatment is controlled to obtain the desired results.

Figure 4:
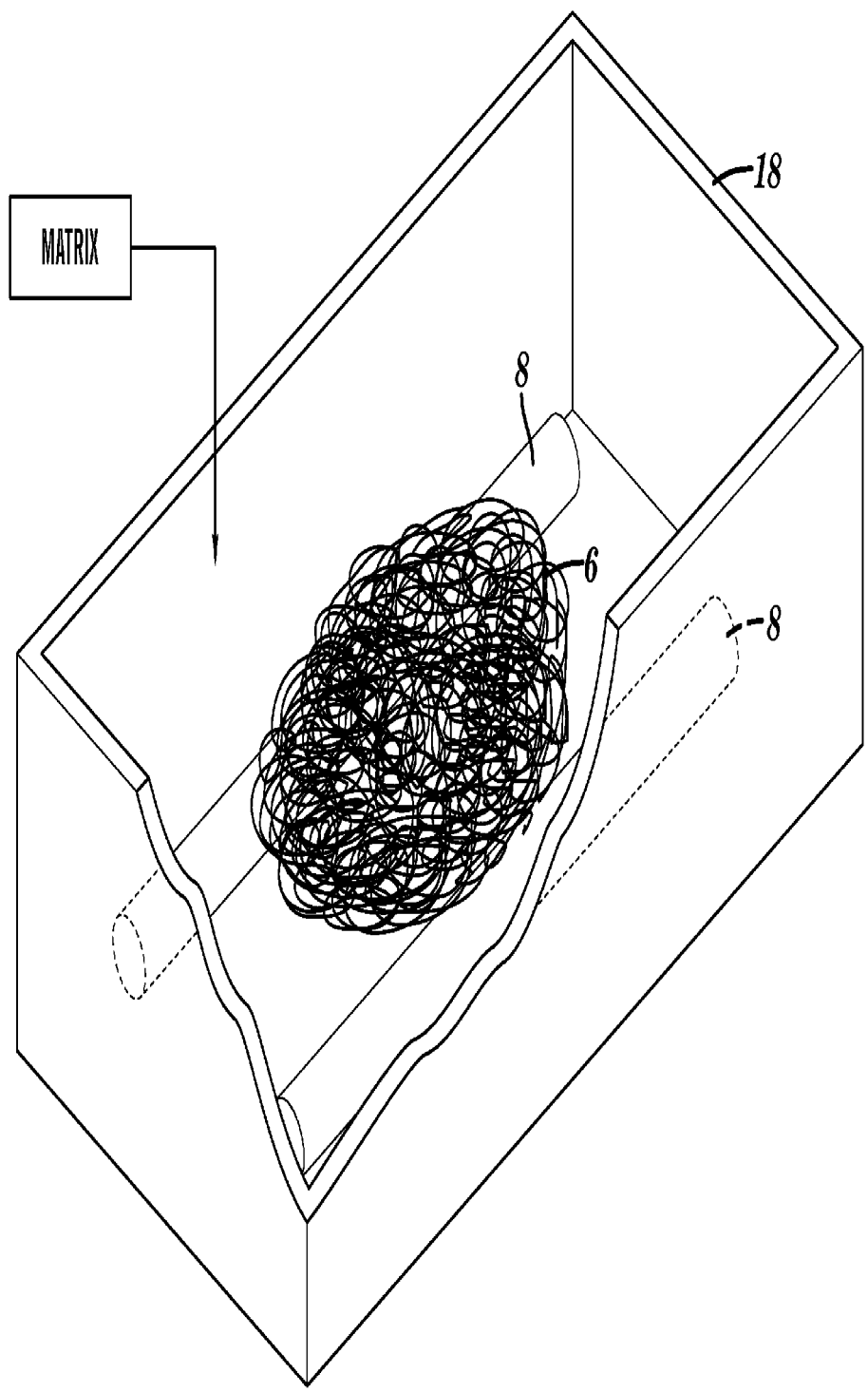
FIG. 4 is a perspective view of the assembly inside a mold before pouring a matrix material. The desired assembly of elongate fibers and elongate structure are placed inside the mold and are, upon introduction of matrix, embedded in the matrix.

Next, fibers 6 in contact with elongate structures 8 are placed in mold 18, as shown in FIG. 4. Matrix material is then poured into mold 18 and allowed to set or solidify. The resulting solid matrix formed around fibers 6 and elongate structures 8 is then removed from mold 18.

Figure 5:
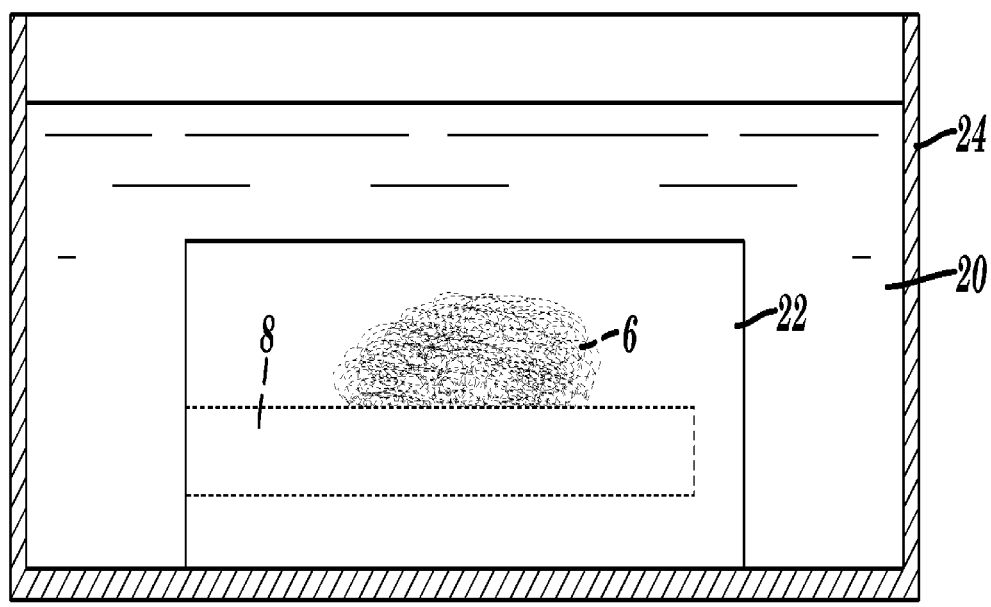
FIG. 5 shows removal of the sacrificial material from the assembly by immersion in an agent useful in dissolving sacrificial fibers.

To remove fibers 6 and elongate structures 8 from solidified matrix, the material forming those components (e.g., sugar) must be sacrificed from the solidified matrix. As shown in FIG. 5, matrix 22 can be placed in trough 24 filled with dissolving agent 20 (e.g., water). This treatment dissolves fibers 6 and elongate structures 8, leaving behind channels in the matrix 22. Dissolving agent 20 is selected to dissolve the sacrificial material forming fibers 6 and elongate structures 8 but not the material forming matrix 22. Other procedures for removing the sacrificial fibers and structures can be envisioned by those skilled in the art. For example, if elongate structures 8 are hollow, dissolving agent can be pumped into them to remove sacrificial material from the matrix.

Figure 6:
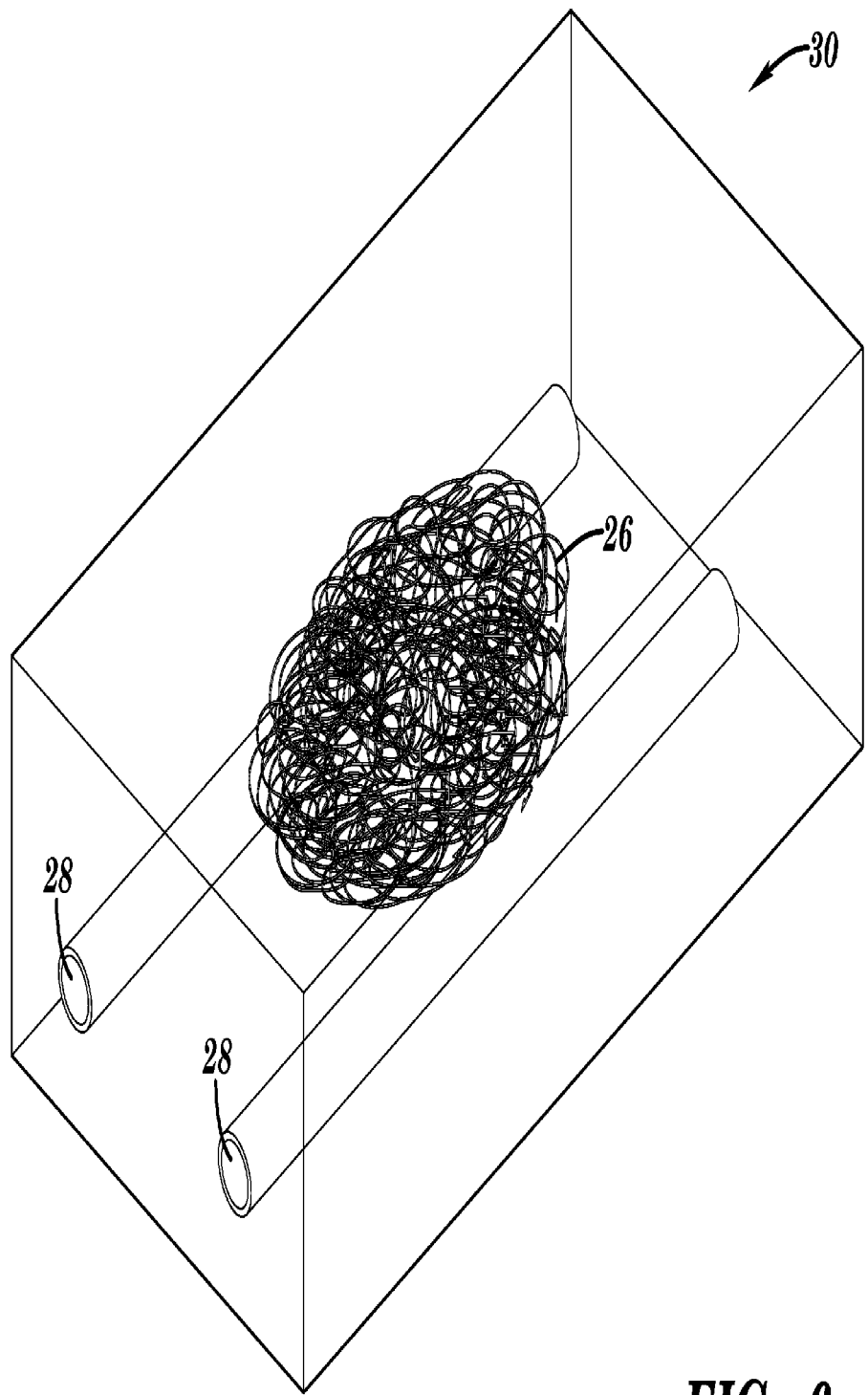
FIG. 6 shows the vascular network preform after the removal of sacrificial material where the fine diameter tubes and elongate passages are formed by sacrificing elongate fibers and elongate structures.
Figure 7:
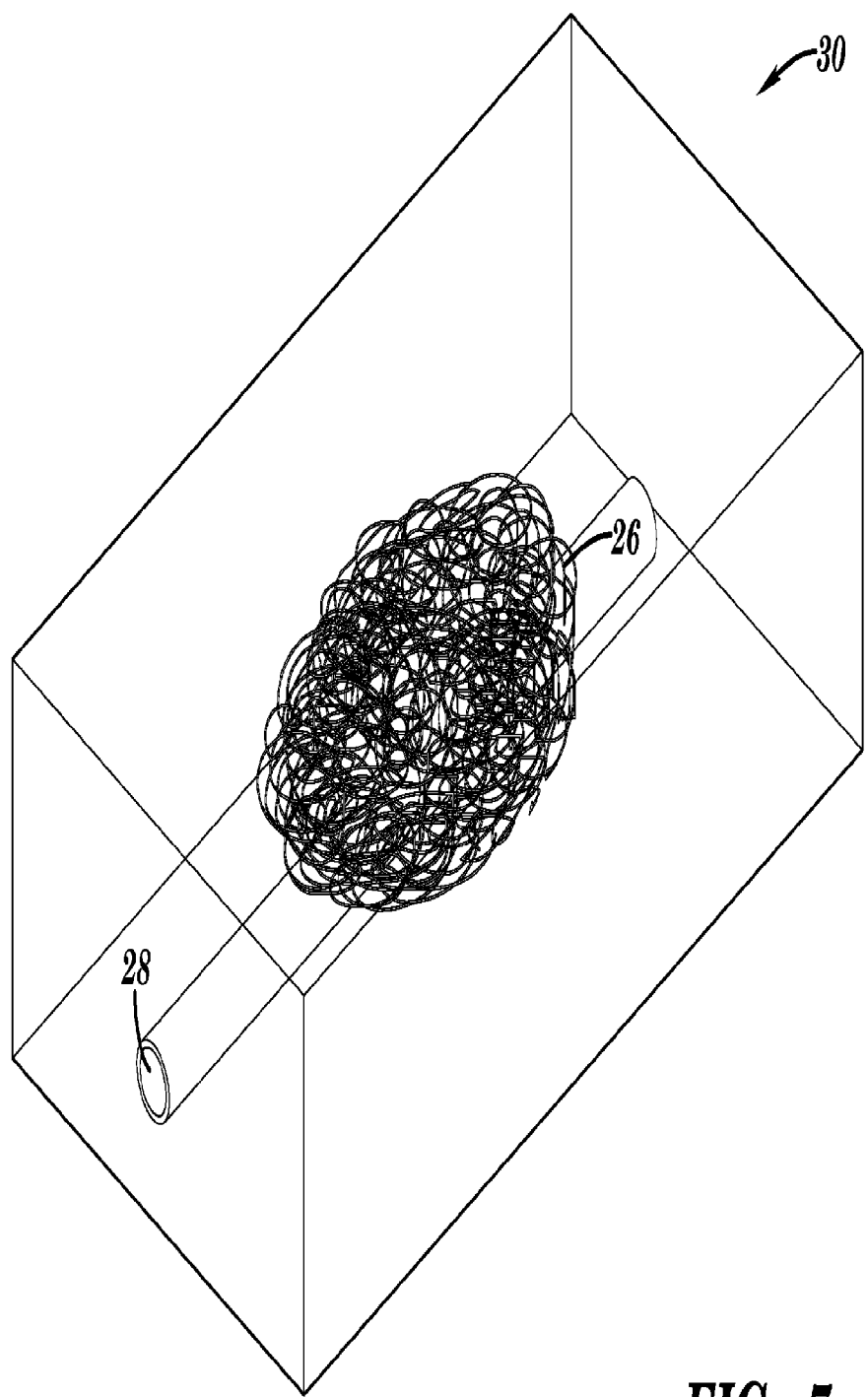
FIG. 7 shows another embodiment of the vascular network preform with one elongate passage.

FIG. 6 illustrates solid preform 30 which results from the above-described process. In particular, solid perform 30 includes elongate fine tubes 26 and elongate passages 28. FIG. 7 shows an alternative embodiment where solid preform 30 has single elongate passage 28 in contact with the fine tubes 26.

One embodiment of the present invention relates to a scalable, rapid, and inexpensive fabrication of a novel 3-dimensional tissue preform containing micrometer size channels (elongate fibers) connected directly to millimeter size inflow (arterial) elongate structure and outflow (venous) elongate structure. The developed fabrication technique involves the use of sacrificial water-soluble fiber structures (e.g., cotton candy and extruded sticks of sugar), over which a polymer material is poured. When the polymer material has solidified, the construct is immersed in water to remove the sacrificial structure, leaving a complex 3-dimensional channel network with a geometry that mimics nature. The millimeter-sized channels could be placed in a predetermined arrangement in order to reproduce the vascular layout of the tissue to be replaced. The resulting vascularized network preform (VNP) containing a three dimensional microtubular network will contain a tubular architecture that mimics that of native capillaries, arterioles and venules in terms of diameter and density within the construct. The average density and size of the capillary channels can also be controlled using this novel engineering approach. Furthermore, the capillary channels will be confluent with a feeding artery and draining vein, both approximately 1 mm in diameter. These larger vessels will act as the vascular pedicle, or leash, for the in vivo applications in which the VNPs can be anastomosed, or connected, to the host vasculature using standard microsurgical techniques. It is this inherent vascularity of the construct which makes it uniquely capable of survival when scaled up beyond several millimeters in size.

When creating a vascular network preform, the spatial organization of the cells within the construct as well as the scaffold material to be used must be taken into account. Tissues are complex structures composed of multiple cell types interspersed in extracellular matrix within a dynamic 3-dimensional microenvironment. Tissue architecture is organized through multimeric adhesion complexes that interact with the cells of the tissue to regulate cytoskeletal organization and activate signaling cascades (Juliano et al., *Annu. Rev. Pharmacol. Toxicol.* 42:283-323 (2002); Yeaman et al., *Physiol Rev.* 79:73-98 (1999), which are hereby incorporated by reference in their entirety). Numerous biological functions, such as tissue development, organ formation, wound healing, and homeostasis, depend on the interaction of cells within a tissue (Edelman et al., *Annu. Rev. Biochem.* 60:155-190 (1991); McDevitt et al., *J. Biomed. Mater. Res.* 60:472-479 (2002); Takeichi, *Curr. Opin. Cell Biol.* 7:619-627 (1995); Zahir et al., *Curr. Opin. Genet. Dev.* 14:71-80 (2004), which are hereby incorporated by reference in their entirety). The specific architecture of cells within a tissue provides cell-cell and cell-extra cellular matrix (ECM) cues that are important in directing these functions. Cells interact with other cells in a tissue through specialized junction molecules, including tight junctions, adherens junctions, gap junctions, and cell adhesion molecules (Zahir et al., *Curr. Opin. Genet. Dev.* 14:71-80 (2004), which is hereby incorporated by reference in its entirety). Thus, appropriate spatial organization and distribution of cells within a tissue is beneficial for preservation of vital cell-cell interactions, including adhesion (Geiger et al., *Annu. Rev. Cell Biol.* 8:307-332 (1992); Lame et al., *Development* 122:3185-3194 (1996); Shibuya et al., *Neuroscience* 67:253-261 (1995), which are hereby incorporated by reference in its entirety), communication, and cell phenotype (Ben-Ze'ev et al., *Proc. Nat'l. Acad. Sci.* 85:2161-

2165 (1988), which is hereby incorporated by reference in its entirety). Not surprisingly, it is believed that the spatial organization of cells within their 3D environment can have an impact on cell fate decisions, such as survival and apoptosis (Zahir et al., *Curr. Opin. Genet. Dev.* 14:71-80 (2004), which is hereby incorporated by reference in its entirety).

In accordance with the present invention, the elongate structures, that are used to form the sacrificial network, can be branched. It is possible for the elongate structures to have different lengths and diameters. The elongate structures can also have varying diameter such that there is a taper, a constriction, or a ballooning of the structure. The diameter of the elongate fibers can be from 1-100 microns and the diameter of the at least one elongate structure can be greater than 500 microns.

The sacrificial fiber network can be designed such that the smaller diameter elongate fibers are attached to medium diameter elongate structures which are in turn attached to larger diameter elongate structures. This sacrificial fiber network is intended to mimic the capillary bed found naturally inside tissues and organs. The design of the vascular network formed by the sacrificial materials can be modified according to the need. For example, the elongate fibers could be laid flat or could be arranged such that they form a three dimensional network. The network fibers could also be embedded in a matrix shaped like a biological organ in order to vascularize the engineered organ and allow ingrowth of cells. The finalized construct can include a biocompatible, and often biodegradable, matrix containing a network of microchannels that span two larger channels or a branching network of larger channels allowing sustained, directional flow between an input channel or channels and an output channel or channels. The average spacing between microchannels will be on the order of 100 microns. The thickness of the construct can range from 500 microns to over 1 cm. The construct may also contain cells on the surface of the channel walls or embedded in the matrix. The construct may be flexible or rigid and may be porous (in addition to having microchannels).

The goal is to provide for constructs with preformed, embedded vascularization. Embodiments of the VNP could be sewn, or anastomosed to the host vessels using standard clinical microsurgical techniques, allowing for immediate vascularization of the entire construct and assuring the survival of cellular constituents within the construct.

The elongate fibers for use in the present invention can be formed by a number of methods well known in the art, including, but not limited to, melt-spinning, wet-spinning, dry-spinning, dry-jet wet spinning, electrospinning, or extrusion (Ziabicki, A. "Fundamentals of Fiber Formation," Wiley, New York (1976); Kroschwitz, J. I., "Encyclopedia of Polymer Science and Engineering. Second Edition, Vol. 6. John Wiley & Sons. New York (1986), which are hereby incorporated by reference in their entirety). Melt spinning is a preferred method of manufacture for fibers of the present invention. The fiber material is usually melted and pumped through a spinneret (die) with numerous holes (one to thousands). The molten fibers are cooled, solidified, and can be collected on a stick or on a take-up wheel. A classic article which discusses structure development during melt spinning is: Dees et al., *J. Appl. Polym. Sci.*, 18:1053-1078 (1974), which is hereby incorporated by reference in its entirety.

Dry spinning also can be used to form fibers from a solution. The fiber material is dissolved in a volatile solvent and the solution is pumped through a spinneret (die) with numerous holes (one to thousands). As the fibers exit the spinneret, air is used to evaporate the solvent so that the fibers solidify and can be collected on a take-up wheel. Stretching of the fibers provides for orientation of the polymer chains along the fiber axis. Cellulose acetate (acetone solvent) is an example of a polymer which is dry spun commercially in large volumes. A more detailed study of dry spinning is provided in Ohzawa et al. *J. Appl. Polym. Sci.*, 13, pp. 257-283 (1969), which is hereby incorporated by reference in its entirety.

Fibers for the purposes of the present invention can also be produced by wet spinning Wet spinning is the one of the earliest process of producing fibers and can be used to make the fibers of the present invention. It is used for fiber-forming substances that have been dissolved in a solvent. The spinnerets are submerged in a chemical bath, and, as the filaments emerge, they precipitate from solution and solidify. Because the solution is extruded directly into the precipitating liquid, this process for making fibers is called wet spinning.

Further, dry-wet spinning is a special process which can be used to obtain high strength or other special fiber properties. The polymer is not in a true liquid state during extrusion. Not completely separated, as they would be in a true solution, the polymer chains are bound together at various points in liquid crystal form. This produces strong inter-chain forces in the resulting filaments that can significantly increase the tensile strength of the fibers. In addition, the liquid crystals are aligned along the fiber axis by the shear forces during extrusion. The filaments emerge with an unusually high degree of orientation relative to each other, further enhancing strength. The process can also be described as dry-wet spinning, since the filaments first pass through air and then are cooled further in a liquid bath. Some high-strength polyethylene and aramid fibers are produced by gel spinning.

Electrospinning can also be used for making fibers of the present invention. The high surface area and high porosity of electrospun fibers allow favorable cell interactions and hence make them potential candidates for tissue engineering applications. It uses an electrical charge to draw very fine (typically on the micro or nano scale) fibers from a liquid. Electrospinning shares characteristics of both electrospraying and conventional solution dry spinning of fibers. The process is non-invasive and does not require the use of coagulation chemistry or high temperatures to produce solid threads from solution. This makes the process particularly suited to the production of fibers using large and complex molecules. Electrospinning from molten precursors is also practiced; this method ensures that no solvent can be carried over into the final product (Doshi et al., *J. of Electrostatics* 35:151-160 (1995); Reneker et al., *Nanotechnology* 7:216-23 (1996); Li et al., *J Biomed Mater Res.* 60:613-21 (2002), which are hereby incorporated by reference in their entirety).

Many sacrificial materials in addition to sugar can be used to make elongate fibers and elongate structures for use in the present invention. Fibrous materials useful in the present invention can be easily determined by a person skilled in the art. Materials which can be easily decomposed or degraded without affecting the surrounding matrix are suitable. Typically, naturally occurring or synthetic fibers or a mixture can be used. For example, without limitation, elongate fibers and the elongate structures can be made from sucrose, polyethylene oxide, polyvinyl acetate, nylon, cellulose, polymethyl methacrylate, bio-degradable fibers such as bast fibers (Flax, Hemp, Jute, Ramie, Kenaf, Abaca), alginate fibers, cellulose, chitosan, protein, hair, collagen, specialty biodegradable fibers, such as lyocell fiber, polylactic acid and poly hydroxyalkanoate and other polymers. Various other suitable fibers and their properties which may be used in the present invention are disclosed in Blackburn et al., "Biodegradable and Sustainable Fibers" Woodhead Publishing Limited (2005); Vasita et al., *Int J Nanomedicine* 1:15-30 (2006); Li et al.,

*Biomaterials* 26:5999-6008 (2005), which are hereby incorporated by reference in their entirety. In a preferred embodiment, sugar is used to make elongate fibers and elongate structures. In certain embodiments, the fibers can be woven together to form elongate structures which have a diameter of 500 µm or greater.

The sacrificing of the elongate fibers and the elongate structure can be carried out by solubilizing in a solvent, by heat decomposition, by reactive gas decomposition, by light decomposition, enzymatic or catalytic degradation or a combination of these techniques. In a preferred embodiment water is used to remove the sacrificial material by immersing the matrix in a water bath. Elevated temperatures can help in dissolving the elongate fibers and the elongate structures making the network.

The sacrificial materials used to form the network of elongate fibers and the at least one elongate structure can be the same or different materials. The materials may be soluble in the same solvent (which is preferable), or two different solvents, or they may be removed using other combinations of the techniques mentioned supra.

Arrangement of elongate fibers can play an important role in guiding regeneration of tissues such as neurons (Yang et al., *Biomaterials* 26:2603-10 (2005), which is hereby incorporated by reference in its entirety) and ligaments (Lee et al., *Biomaterials* 26:1261-70 (2005), which is hereby incorporated by reference in its entirety). It is also desirable to orient the fibers if there is a need to control the direction of flow of fluids (e.g., blood flow or flow of cell culture medium). In engineered tissue constructs, the orientation of elongate fibers could be used to connect and direct the flow of blood from the incoming arteriole or artery to outgoing vein or venule. In bioreactor applications, it would be desirable to control the direction of flow in order to transport products to, for example, a separate compartment or a separate feed or delivery line. The network of elongate fibers and the at least one elongate structure can be oriented before or after placing them in contact with one another. Techniques such as mechanical stretching or combing of the fibers in both molten and solid states could provide for orientation of the fibers along a desired axis.

The network of elongate fibers and the at least one elongate structure, which are in contact with another, are preferably welded or connected together to form an interconnected network. The larger elongate structure is contacted with the elongate fiber network and the two are welded together using heat, humidity, cross linking, or other techniques. For example, network fibers and elongate structures can be placed in an oven for an optimal amount of time to melt the fibers and fuse them together. Care should be taken to preserve the structure and connectivity of the microfiber network, and one should avoid exposing the sacrificial structure to conditions that may degrade it, such as high humidity or extremely high heat environments.

In one embodiment of the present invention, the method of applying a matrix comprises applying a flowable material around the network of elongate fibers in contact with the at least one elongate structure and allowing the solidifying of the flowable material to form a solid matrix. The matrix is then allowed to harden via cooling, polymerization, crosslinking, photo induced polymerization or crosslinking, or solvent evaporation, which are well known in the art. The sacrificial structure (which is made of elongate fibers and elongate structures) is thus embedded in a solid matrix. The sacrificial structure is later removed by immersing the entire structure in a solvent that dissolves the sacrificial structure but not the polymer matrix or by exposing it to any other degradation techniques, as mentioned supra.

The matrix of the present invention may be any polymer, including, but not limited to, polydimethylsiloxane, polyglycerol sebacate, polycaprolactone, polylactic acid, polyglycolic acid, cellulose, alginate, agar, agarose, collagen I, collagen IV, hyaluronic acid, fibrin, poly-L-lactide (PLLA), poly (lactic-co-glycolic acid) (PLGA), or another suitable material. These materials provide maximum control of degradability, manageability, size, and configuration. The matrices must have sufficient surface area and exposure to nutrients in order to support healthy growth of cells and differentiation. The configuration of the tissue constructs should also allow for continued and sustainable supply of nutrients, continued blood vessel ingrowth, sites for attachment of living cells, and removal of waste products. In vitro cell viability and cell attachment to matrix can be assessed by, for example, scanning electron microscopy, histology, fluorescence microscopy, confocal microscopy and other quantitative biochemical or cellular assays.

Bulk properties of the matrix can be controlled by appropriately choosing the matrix material. Optimal biomaterials with which to fabricate the matrix can be determined experimentally. Preliminary studies have been conducted largely with polydimethylsiloxane (PDMS), a biocompatible but non biodegradable silicone polymer which does not allow for vascular ingrowth from the host tissues. Several commonly available biocompatible and biodegradable polymers can be examined for mechanical stability and compatibility with the microchannel fabrication process. The mechanical properties and degradation timescale of many of these materials can be tuned by choosing the appropriate molecular weight and/or crosslinking density. Furthermore, the fabrication technique of the present invention will allow for polymeric mixtures as well as the fabrication of constructs with specifically layered structures (e.g., collagen IV lining tubules in a construct made from PLLA). For example, endothelial progenitor cells (EPCs) can be harvested from donor syngeneic animals and infused into the VNP via the arterial pedicle. After allowing for the EPCs to settle within the vascular framework, the VNPs can be connected to a bioreactor and cell culture media can be circulated to allow the EPCs to grow to confluence within the vascular network. VNPs can then be examined at various time points to demonstrate cellular viability and integrity of structure.

The matrix or support structure is desirably a biodegradable polymer so that it eventually degrades when implanted or used in vivo. Preferably, the polymer is degraded by hydrolysis at a controlled rate and can be reabsorbed. In some embodiments, this matrix can be in contact, embedded, or overlaid with a second matrix of similar or different properties. The second matrix could incorporate compounds or cells which are, for example, incompatible with the first matrix but can leech into or grow inside the first matrix. In other words, several matrices with desired properties could be used in one preform without limiting the potential applications.

A porogen can be added to the matrix before or after the solidifying of the matrix under conditions effective to introduce pores into the preform. The process could also involve combining sacrificial nanofibers or fibers for physical support with porogens and embedding within the matrix to form structures that mimic the extracellular matrix (Zhang et al., *Journal of Biomedical Materials Research* 52:430-438 (2000), which is hereby incorporated by reference in its entirety). Porogens and nanofibrous scaffolds are added in addition to the sacrificial elongate fiber and elongate structures in order to develop systems with high porosity and greater diffusion rates. Increased porosity allows for easy diffusion of nutrients and waste products. Sacrificial nanofibrous fibrous scaffolds embedded in polymer matrix can further act as basement membranes over which cells can attach and spread. The porogen can be incorporated in the polymer matrix and can be later sacrificed such that it leaves spaces through which fluids could seep deeper into the preform or act as additional surface area for cells to attach. Biodegradable porous preforms could be used to decrease the amount of matrix material that is implanted into a host or patient so that there is less waste product generated upon in vivo degradation of the matrix. This could enable early degradation of the biodegradable solid preform by providing deeper access to degrading enzymes, reducing the total weight of tissue implants, and limiting the side effects of the degradation byproducts in the host.

A drug and/or a biochemical agent can be added to the matrix before or after the solidifying of the matrix. Various drugs and/or a biochemical agents may be incorporated into the matrix for slow release by diffusion or during the degradation of the matrix. These agents include any chemical or biochemical compound which is compatible with the matrix. For example, the drug includes, but is not limited to, chemical compounds, polymerization agents, catalytic agents, enzymes, nutrients, growth factors, inducers of differentiation or de-differentiation, products of secretion, immunomodulators, inhibitors of inflammation, regression factors, biological factors which enhance or allow ingrowth of the vascular, muscular, lymphatic or neural tissue. These drugs or biochemical agents can be incorporated into the vascularized matrix or incorporated into a separate matrix superimposed, embedded or in contact with the vascularized matrix such that there is exchange between the matrices. These drugs or agents could also be incorporated in an encapsulated form which, for example, delays the release of the agent or drug, triggers the release of the agent or drug when an injury occurs, or releases the drug or agent when the surrounding matrix is dissolved or degraded.

The preform can contain a vascularized network of fine diameter tubes in contact with at least one elongate structure seeded with incubated cells. Typically, once the sacrificial structure is removed, the polymer matrix will contain a microchannel network. This channel network can be seeded with biological cells by injecting a cell-containing solution or culture and incubating the construct. There are many means of seeding the channels. For example, cells are incorporated into the matrix by pre-immersion or post-immersion, by incorporating cells in the elongate fibers pre-fabrication, by incorporating cells in the solvent used to remove the sacrificial materials, or by inoculating the matrix with cells.

Cells of one or more types can be seeded into and grown on the preform. The preform structure, the length of time, and the conditions under which the cells are cultured or grown are determined on an individual basis for each type of cell. The optimal conditions can be determined by, for example, measuring cell attachment (only viable cells remain attached to the matrix polymer), extent of proliferation, and measuring cellular function or secretion. Examples of cells which can be used include endothelial cells, smooth muscle cells, cells from various organs (e.g., thyroid, pancreas, skin, muscles, heart, kidney, lungs, liver, brain, spine, and gonads). In a preferred embodiment, the cell seeded monolith is seeded with endothelial cells. For example, the channel walls of the cell seeded monolith can be lined with endothelial cells.

The cell seeded monolith of the present invention can be implanted into a subject via anastomosis between at least one native artery and vein, with the at least one elongate passage extending from each, using standard microsurgical techniques. The cell seeded monolith can also be used for ex vivo drug testing, cell assays. One example of such a use is where cancer cells are seeded into the monolith and chemotherapeutic agents are caused to pass through the monolith.

Another aspect of the present invention is directed to a solid preform comprising a solid matrix, a vascular network of fine diameter tubes randomly extending in a non-repeating pattern within the solid matrix, and at least one elongate passage having a diameter greater than that of the fine diameter tubes. The at least one elongate passage extending within the solid matrix is in contact with the vascular network of fine diameter tubes.

The fine diameter tubes in the solid preform are desirably enmeshed. By enmeshed it is meant that the fine diameter tubes are entangled and connected to each other at numerous random places. They are generally surrounded by the matrix in each direction and the matrix fills the outside spaces between adjacent tubes. The tubes can extend in any direction and do not form any repeating patterns.

In another embodiment, the elongate passages in the solid matrix are branched. In general, the passages and the microchannel network formed by the fine diameter tubes can be designed in any configuration as desired. Any number of branched and elongate passages and networks could be designed into the solid preform by making a sacrificial fiber and sacrificial elongate structure network. An advantage of this invention is the flexibility in the configuration and the ease of design.

The passages and the microchannel network in the solid preform are formed after the sacrificial materials have been removed. The diameter of fine tubes and the elongate passages is proportional to the diameter of the sacrificial elongate fibers and sacrificial elongate structures. The polymer of the matrix could account for some shrinking or expansion of the diameter depending on its properties. In one embodiment, the diameter of the fine diameter tubes is in the range of 1-100 microns and the diameter of the elongate passages is 500 microns or greater.

The solid preform can be made of a solid matrix which is a polymer. The configuration and the materials used to produce the solid perform are fully described above.

The solid preform may be made of a solid matrix that is sealed so that fluids can only enter the solid preform through the at least one elongate passage. It is also possible to construct the solid preform in manner such that the fluids are given a directional flow. In one embodiment, the solid preform comprises at least two elongate passages, with at least one of the elongate passages being configured to permit entry of fluid in said vascular network and at least one of the elongate passages being configured to permit fluid to be withdrawn from said vascular network. For example, the fluids could be distributed within the solid preform by designing a branched passage connected to two or more networks or designing a sealed construct where the fluids enter by one passage, are distributed through the network of fine micro channels, and then exit by another passage. This type of construct, in a biological system, would enable an increase in the surface area that comes in contact with the blood, or in a heat exchange system, would enable efficient heat exchange with the surrounding materials.

In one embodiment, the solid preform can include a catalyst suitable to convert a healing agent to a filler at sites of injury or cracking in the solid preform. The healing agent can be located in microcapsules within the solid preform or flowing through the microchannel network.

The solid preform can be configured such that there is transfer of heat between the solid matrix and a fluid present in the vascular network. The solid preform materials are able to withstand working temperatures, capable of being rapidly heated or cooled, and can be encased in a non conducting material to minimize losses. The vascular network within the solid preform can be filled with a fluid which has desirable properties (e.g., high heat capacity, capable of temperature dependent color change, high thermal conductivity, suitable viscosity, and useful expansion/contraction properties).

In one embodiment, the solid preform is porous which can be achieved by introducing a porogen as described supra.

Sometimes, it may be desirable to introduce larger cavities or molded spaces into the preform, for example, the preform could be designed such that it mimics the aortic and ventricular cavities found in a biological heart. The combination of elongate passages, microchannel network, and molded porogens will enable unprecedented tissue design capabilities without the limitations posed due to an absence of micro capillary networks, leading to inadequate supply of nutrients and blood as well as an absence of support architecture and cell attachment sites.

Another aspect of the present invention is directed to a method of treating a patient for a condition requiring vascularization. The method includes providing the above-described cell seeded monolith, selecting a subject with a condition requiring vascularization, and implanting the cell seeded monolith into the selected subject.

This method can be used for wound healing, organ transplantation, tissue transplantation, and burn treatment.

Microsurgical experiments can be used to connect the tissue construct to the host animal's or animal model's vascular system. This arrangement can be used, for example, to determine whether an endothelialized construct is non-thrombogenic and if it can maintain long term patency. Furthermore, the tissue construct will become populated with multiple cell types from the host (fibroblasts, smooth muscle cells, etc.). Angiogenesis and vasculogenesis are expected to continue within the tissue construct in the relatively ischemic areas between endothelialized channels.

The viability of the VNPs can be determined in vivo in animal models. Utilizing the processes of angiogenesis and vasculogenesis, the optimal conditions to generate vasculature within the engineered VNP can be determined. The sine qua non of neovasculogenesis is the mobilization and recruitment of pro-angiogenic marrow-derived endothelial (VEGFR2+) and hematopoietic (CXCR4+VEGFR1+) cells. The unique fabrication technology of the present invention allows formation of extremely dense networks of interweaving channels with diameters on the micron to tens (hundreds) of microns scale. As these channels can be connected to larger vessels, cells can be injected into the system simply by flowing a solution of cells into the elongate structures which can act as an "artery" and out of the "vein". These cells can adhere to the walls of the micro- and macrovascular architecture of the fabricated vessels and thereby produce a full biological vascular network, allowing for anastomosis, and perfusion without thrombogenesis. Cell adherence in this three dimensional tissue construct may be promoted by incorporation of the optimal stoichiometry, which can be experimentally determined, of cells, proangiogenic cytokines (such as VEGF, bFGF, P1GF, MMPs) and chemokines (such as SDF-1 and FGF-4). The initial optimization step will involve injection of cells (e.g., endothelial cells and hemangiocytes) into the supporting solid preform and incubating the cells to produce a cell seeded monolith. It has been demonstrated that hemangiocytes are capable of releasing pro-angiogenic factors, such as angiopoietin-2, to promote neovascularization. Aliquots of the conditioned medium (every 24 hours) can be serially collected from the bioreactor. The composition of proangiogenic cytokines released in paracrine can be determined using commercially available ELISA Kits (Quantikine, R&D) for VEGF-A, P1GF, MMPs, bFGF, SDF-1, and angiopoietins. The cell dose to optimize neovascularization can also be optimized. If needed, an exogenous cocktail of pro-angiogenic cytokines/chemokines can be added to the bioreactor to promote growth and remodeling of the vascular niche within the monolith. The definitive histomorphology of the monolith to be used as a tissue construct can be studied by hematoxylin/eosin staining of sections as well as by immunohistochemistry for CD31 (PECAM1), VEGFR1, VEGFR2, and CXCR4.

To assess in vivo short term and long term viability and durability, the prefabricated vascularized tissue constructs can be placed in host animals. After determining the optimal stoichiometry of the VNP components, endothelialized VNPs can be anastomosed, or connected to host animal's recipient vessels. Small animal models, such as rats can be used, as their femoral artery and vein are approximately 1 mm in diameter, which is the designed diameter of the VNPs vascular pedicle. The artery and vein of vascular leash of the VNP can be sewn to the rat femoral artery and vein using standard microsurgical technique with the aid of an operating microscope. Immediate perfusion and viability of the VNPs will be demonstrated. Animals can be examined after implantation to re-expose the VNP and demonstrate patency of the vascular pedicle. In vivo assessment of artificial tissue viability can be made by standard gross observation (i.e. color, bleeding in response to pinprick, signs of incorporation and healing into surrounding tissues) as well as serial measurements of: a) the degree and stability of the vascular network and construct integrity by micro-CT and b) patency and perfusion of the construct (by Laser Doppler perfusion scan). The definitive histomorphology of the incorporated construct can be studied by hematoxylin/eosin staining of tissue sections as well as by immunohistochemistry for CD31 (PECAM1), VEGFR1, VEGFR2, and CXCR4 as described supra. Animals in the experimental groups can be followed for a certain time duration (e.g., as long as 3 months) in order to evaluate the durability and functionality of the tissue construct in vivo.

In addition to fabricating artificial implantable microvasculature, there are several other applications for complex three dimensional microfluidic networks. Unlike self-healing polymer systems that rely on microcapsules containing healing agents (White et al., *Nature* 409:794-797 (2001), which is hereby incorporated by reference in its entirety), materials containing artificial vascular systems that supply healing agents (from a distance) to cracks are able to heal in the same location multiple times (Toohey et al., *Nat. Mater.* 6:581-585 (2007), which is hereby incorporated by reference in its entirety). Due to the high density of channel intersections and tortuous paths, mixing of multiple input fluid streams is efficiently accomplished in artificial vascular systems (Therriault et al., *Nat Mater* 2:265-271 (2003), which is hereby incorporated by reference in its entirety). The vascular network preforms of the present invention can also be used for drug delivery (Saltzman et al., *Nat Rev Drug Disc* 1:177-186 (2002), which is hereby incorporated by reference in its entirety) and may be useful for supplying drug-containing fluid to a wide area or volume of tissue. Artificial vascular networks seeded with cells could be used ex vivo for drug development, allowing researchers to study the behavior of drugs or toxins on cells in a biomimetic environment (Viravaidya et al., *Biotechnology Progress* 20:316-323 (2004), which is hereby incorporated by reference in its entirety).

Microfluidic networks inside materials may also be used to change an object's appearance (by injecting colored or index-matching fluid) or to heat or cool an object internally. Finally, artificial microfluidic systems can be used to study natural fluidic systems (Wheeler et al., *Nature* 455:208-212 (2008), which is hereby incorporated by reference in its entirety).

The present invention is also directed to a method of forming a self healing material system. This involves providing the above-described solid preform and allowing for the releasing of the healing agent from the vascular network upon injury to or cracking of the solid perform. As a result, the injury or crack is filled.

In these systems, a healing agent is contained either in a plurality of microcapsules dispersed in the solid matrix or flows within the vascular network of the solid preform. When the substrate experiences a dramatic force that causes fractures or cracks, the healing agent is exposed to the rupture site and acts to repair the damaged area. Healing agents include catalysts, which will induce polymerization and cross linking in the damaged area, or solvents, which weld cracks closed. The benefit of using a vascular system in a self-healing material is that the healing agent may be delivered from a distance, and may be refreshed, eliminating the problem encountered when using microcapsules with a finite supply of healing agent near the damaged area. Prior known self-healing polymer systems utilize vascular networks employing channel networks fabricated using three dimensional fabrication techniques based on inkjet technology. These involve rapid prototyping which is relatively slow and not scalable compared to the sacrificial fiber techniques of the present invention. The inherent vascularity of the constructs of the present invention designed as artificial tissues could also be used to supply the polymer matrix with a healing agent.

Figure 8:
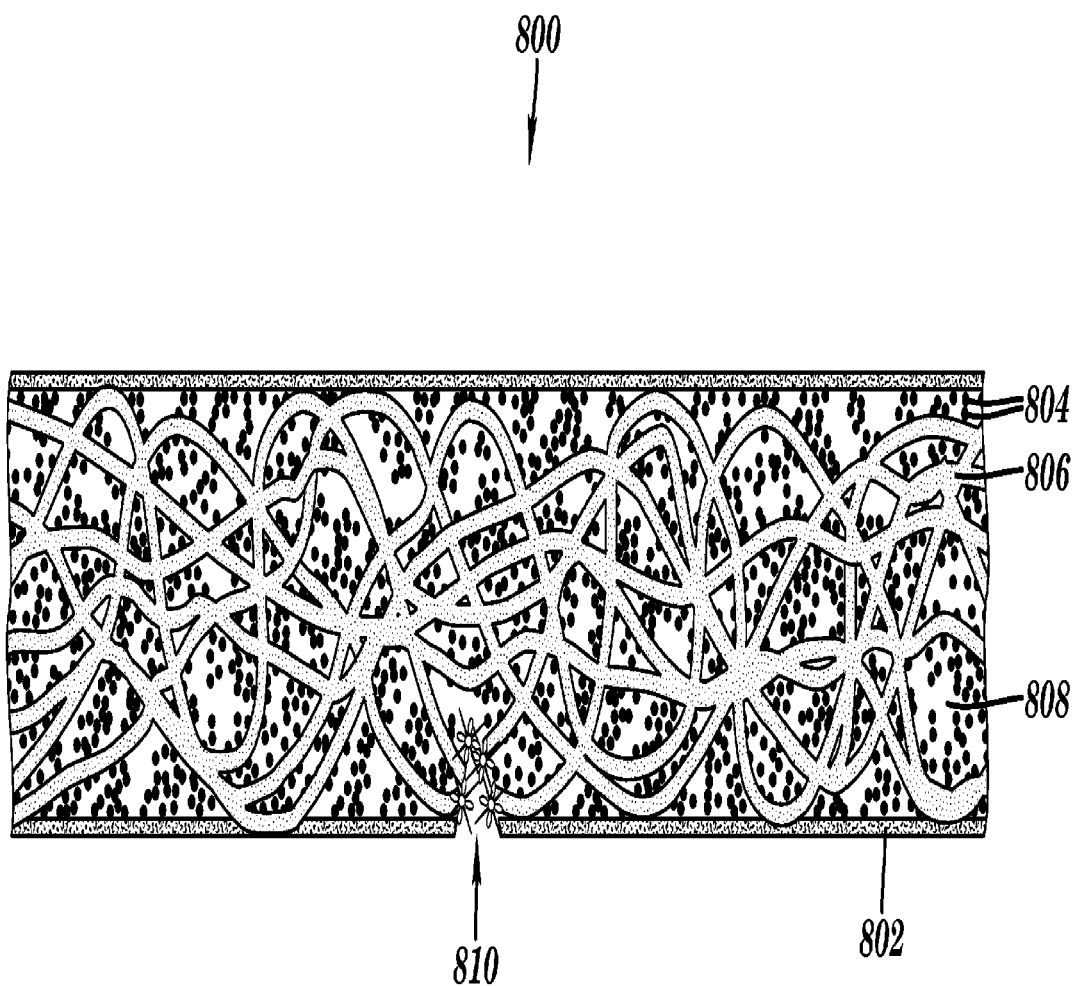
FIG. 8 shows a cross-sectional view of a self healing, vascular network preform. The channels can be provided with a healing solution that is protected from the catalyst particles embedded in the material. When the material fractures, the catalyst particles are exposed to the healing solution, and a chemical reaction occurs. As a result, any injury site is healed.

FIG. 8 is an illustration of a self healing polymer system 800 made from the solid preform 802 of the present invention. Solid perform 802 is provided with dispersed catalyzing agent 804. Healing agent is flowing through or contained in vascular network 806. Upon injury, for example, at site 810, healing agent from vascular network 806 is exposed and polymerizes (catalyzed by exposed catalyzing agent 804) at injury site 810. As a result, injury site 810 is filled and repaired.

Another aspect of the present invention is directed to transferring heat to a surface or volume. This involves providing the above-described solid preform which is configured such that there is transfer of heat between the solid preform and a fluid present in the vascular network. The fluid is passed through the vascular network so that the solid preform heats or cools the fluid or the fluid heats or cools the solid preform.

In one embodiment, the solid preform may be supported within a device having a first access port and a second access port with the microchannels coupling the access ports. The ports can be used to provide and remove fluids to and from the matrix.

In an alternative embodiment, the fluids change color with temperature. For example, the fluid can be darker when cooler and lighter when warmer. As the fluid moves through the matrix, it can be warmed or cooled. Due to the color change, the matrix can be designed to display color and, as a result, indicate the temperature of the fluid. In another embodiment, colored fluids could be introduced into the vascular network and used to change the color of the matrix. This could be, for example, used in design of materials which change color in response to changing surroundings, for camouflage.

Figure 9:
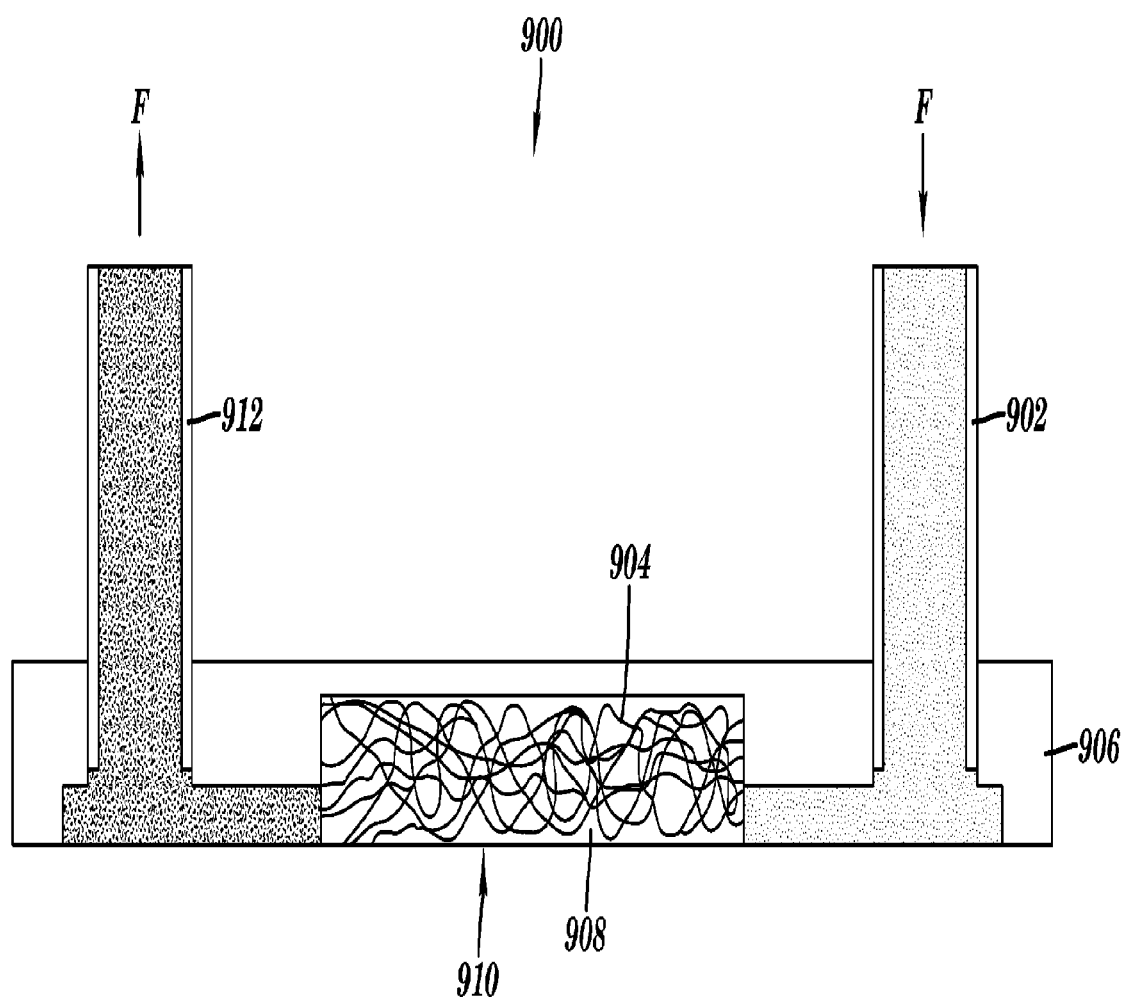
FIG. 9 is a schematic diagram, showing the use of the vascular network preform of the present invention as a heat exchanger.

As shown in FIG. 9, heat exchange system 900 includes solid perform 910 made from matrix 908, with vascular network 904, and (optional) insulation 906. Access ports 902 and 912 are connected through vascular network 904 in solid perform 910. Access port 902 receives fluid F and access port 912 discharges fluid F after it has passed through vascular network 904. Fluid F can change color after passing through solid preform 910. In separate embodiments, a desired temperature can be achieved by maintaining the temperature of solid preform 910 at a set value to heat or cool fluid F or by maintaining the temperature of fluid F (as it enters vascular network 904) at a set value to heat or cool solid perform 910.

Figure 10:
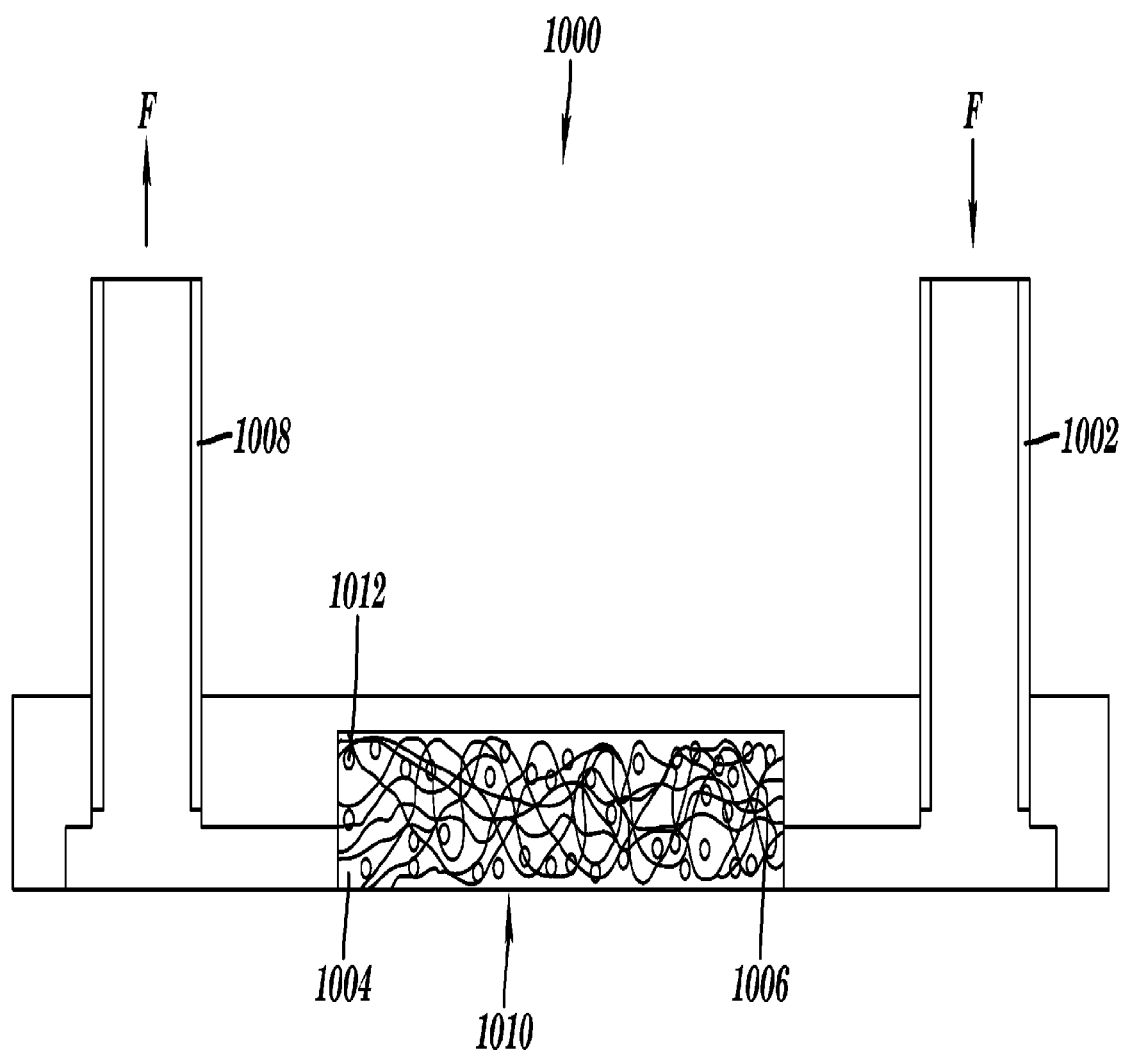
FIG. 10 is a schematic diagram, showing the use of the vascularized network perform as a bioreactor.

The present invention also relates to a method of carrying out a biological reaction. The above-described cell seeded monolith is provided and fluids are passed through the cell seeded monolith under conditions effective to carry out the biological reaction. FIG. 10 is a schematic of bioreactor system 1000 having monolith 1010 which is preseeded with cells 1012, which are provided with an environment suitable for growth and production of a biological agent. Monolith 1010 is connected to access ports 1002 and 1008 by vascular network 1006, which is embedded in a matrix 1004. In one embodiment, fluid F can enter access port 1002 and be discharged through access port 1008. Alternatively, both of these ports can feed or discharge material. Access ports 1002 and 1008 can be used, respectively, to provide the cells with nutrients and to remove metabolic waste products or useful products made by cells.

Bioreactors formed using the 3-dimensional VNPs of the present invention can be used to grow cells for a variety of applications, for example, fermentation, animal cell culture, tissue engineering, and waste water treatment. Bioreactors for carrying out fermentation or cultivation of cells of animals or plants may include a bed type which is formed of the vascularized network preform of the present invention. The vascular network can be used, for example, to provide for cell immobilization, nutrient transport, protection against shear forces, high physical strength support for tissue architecture, and connecting various dispersed fine tubes to a single or multiple feed or product lines.

Microfluidic bioreactors have been shown to be valuable for various cellular applications. Microchannels can be used to protect sensitive cells from the detrimental effects of fluidic shear stress. For example, microchannel network bioreactors are highly beneficial for the culture of human embryonic stem (ES) cells and can be used for ES cell biology studies and ES tissue engineering applications (Korin et al., *Biomed Microdevices* 11:87-94 (2009); Korin et al., *Biotechnol Bioeng.* 102(4):1222-30 (2009), which are hereby incorporated by reference in their entirety).

In one embodiment, the biological reaction produces a biochemical agent or molecule. Because of the need to culture mammalian cells in the laboratory in large quantities, bioreactors with the vascularized preform can be an important tool in research and production of cells that produce active or recombinant proteins. One use of the bioreactor of the present invention is where large numbers of cells are grown to refine the minute quantities of an active material (e.g., proteins) that the cells might secrete. Another use of bioreactors is the scale-up of laboratory cell culture processes for commercial purposes to mass produce active proteins made by genetically engineered cells. The bioreactor can comprise cells or cellular materials which are used for example, but not limited to, to treat a disease.

The biological reaction can be an assay to determine the effect of a drug or biochemical agent on the cells seeded within the monolith.

EXAMPLES

Example 1

Sacrificial Microfiber Fabrication

To form the microchannels, melt-spun sugar fiber networks were produced using a modified cotton candy machine (The Helman Group, CCM-505). The cotton candy machine was modified to allow the user to exert more control over the process parameters. Store-bought granulated sugar was used in the machine. The heaters and the motor were each connected to variacs in order to control the extractor head temperature and rotational speed. The channel diameter and channel density may be controlled by varying the melt-spinning apparatus extractor head speed and temperature and by varying the fiber collection technique and subsequent handling, respectively (Bursac et al., *Biochem. Biophys. Res. Commun.*, 361:847-853 (2007), which is hereby incorporated by reference in its entirety). The temperature of the extractor head was not varied from the default setting. Only 90V were supplied to the extractor head motor (as opposed to the line voltage), causing it to spin slower and produce qualitatively larger, stiffer fibers. The fibers were collected manually according to the machine instructions.

Example 2

Sugar Stick Fabrication

Sticks of sugar were formed by pouring molten sugar onto aluminum foil. First, store-bought granulated sugar was melted in a beaker using a hot plate at approximately 190° C. The sugar was removed from the heat before it burned. The molten sugar was manually poured into thin lines on aluminum foil. The speed with which the molten sugar was dragged along the foil determined the sugar stick diameter. The molten sugar cooled quickly at room temperature, and could then be used as a sacrificial material to make macrochannels.

Example 3

Assembly

The sugar sticks were embedded into the microfiber ball by hand. If the ambient humidity was not high enough to render the sugar sticks sticky, they were brought near running hot water to put them in a more humid environment. The sugar sticks were placed on the microfiber ball in the desired location, and the microfiber ball was then manually pressed into an appropriate size to fit in a Teflon mold.

Example 4

Design and Fabrication of the Three-Dimensional (3D) Nascent Vascular Network within a Biocompatible Polymeric Construct The fabrication technique is based upon sacrificial microfiber networks that provide the structure to form capillary networks. Standard melt-spun sugar fiber networks, produced using a cotton candy machine, are of a size and density comparable to that of capillary networks. The size and density of these channels can be adjusted by changing the temperature and rotational speed of the cotton candy machine extractor head, modifying the collection technique, or changing the sacrificial material.

Sacrificial structures with macroscale sizes of different length, shapes, and diameter, used to form arteries and veins, can be produced by extruding sugar cylinders using standard polymer extrusion equipment. These larger structures are inserted into the cotton candy network, and the whole sugar structure is "welded" at the contacts between individual sugar strands by placing it in an incubator for a short period of time (i.e. a few minutes) to weld the microfibers to the larger structure. To form fluidic inlet and outlet macrochannels, sticks of solid sucrose formed by pouring molten sugar were used. The size of the sticks determines the size of the channels. Therefore, sticks with diameters on the order of 1 mm (the lower limit of vessel diameter that can be reliably sutured and be expected to remain patent) were made. Short sections of the sugar sticks were inserted into balls of sucrose fibers, and this sugar structure was placed in an incubator for ~2 minutes to "weld" the individual sugar structures together.

The sugar was then placed in a Teflon mold, and PDMS (Sylgard 184, Dow Corning) that had been mixed at a resin:hardener ratio of 10:1 and degassed was then poured over the sugar. The devices were then allowed to cure for 24 hours at room temperature. After curing, the devices were placed in a bath of water and ethanol at 70° C. for several days to dissolve away the sugar structure, leaving a microchannel network inside the PDMS matrix.

Epoxy constructs were formed by pouring a degassed mixture of hardener and resin (Everfix 100642, Evercoat) over sugar structures before the epoxy had cured. Polycaprolactone (PCL) (Aldrich, 14,000 MW) constructs were formed from a polymer melt at ~70° C. poured over sugar structures, left in a 70° C. oven to allow the polymer to fully coat the sugar, and finally allowed to cool at room temperature. PCL devices were immersed in a water/ethanol bath at 50° C. to ensure the polymer matrix did not melt.

Figure 11:
FIG. 11 shows an image of a polydimethylsiloxane (PDMS) construct after flowing blood through it.

Any desirable polymer resin or solution, as per the use and requirement, can be poured over the sugar structure. When the resin has cross linked (or solvent has evaporated from the solution) and the polymer is a solid structure, the sugar structure can be removed by placing the entire piece in warm water for several days (often ethanol is added to prevent growth of organic materials). The final product after this fabrication process is shown in FIG. 11. The constructs fabricated using the technique outlined above can range in thickness from under one millimeter to several centimeters.

Example 5

Channel Diameter

Figure 12A:
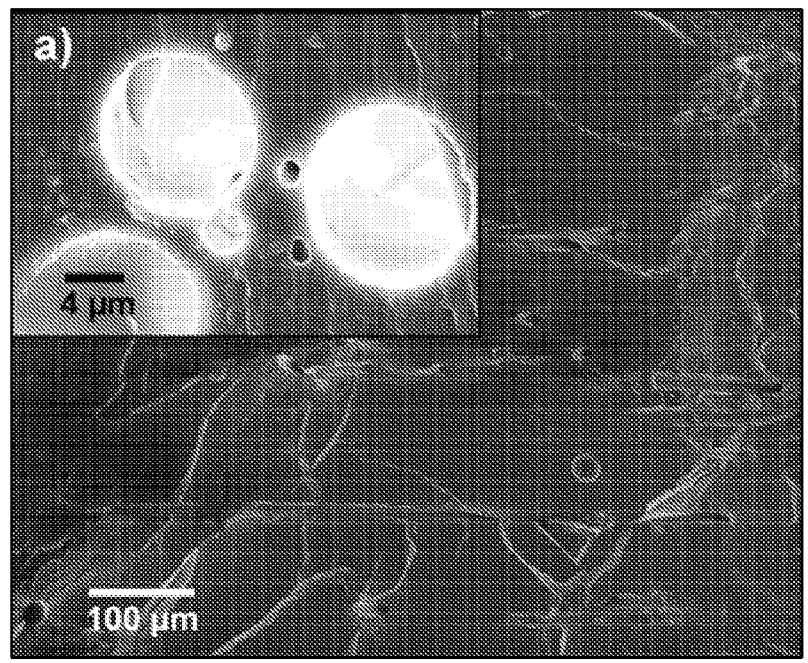
FIGS. 12A-B show cross-sectional images of the vascular network perform of the present invention.
Figure 12B:
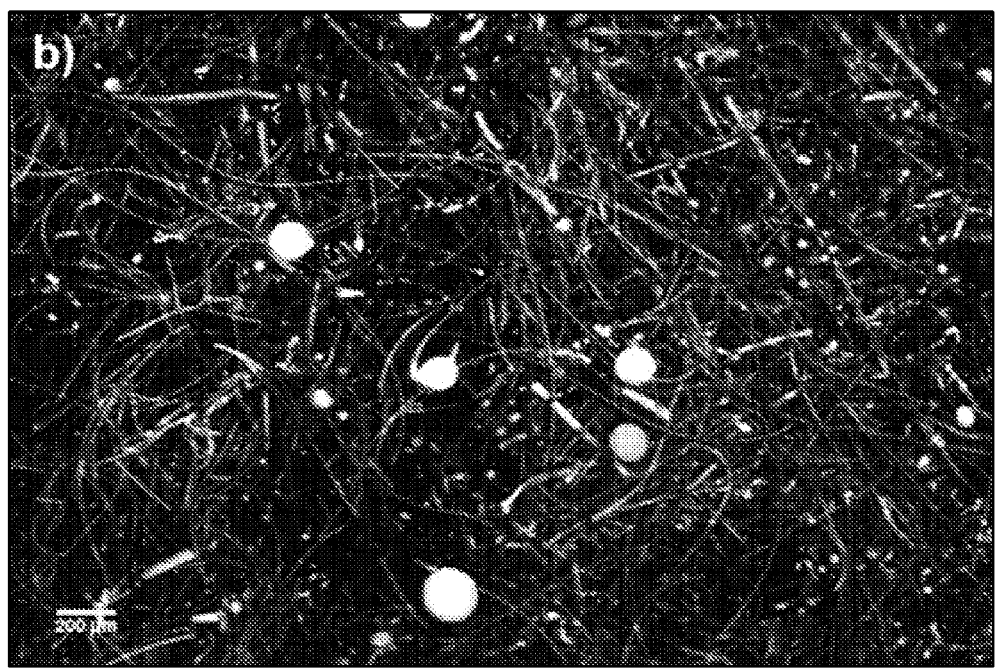

To fully explore the range of channel diameters, scanning electron microscopy (SEM) (Leo 1550) was used to image cross sections of PDMS devices (FIG. 12A). From the SEM images, it was concluded that the channel sizes were approximately 1-100 μm, and the separation between channels was a few hundred microns. These parameters are similar to those of natural capillary beds (R. A. Freitas, *Nanomedicine* (1999), which is hereby incorporated by reference in its entirety). To further image the 3D extent of the microchannel networks, multiphoton microscopy was employed using a homebuilt system (Kloppenburg et al., *J. Neurosci.* 20:2523-2533 (2000), which is hereby incorporated by reference in its entirety) to image a PDMS construct filled with 175 μM fluorescein dye (FIG. 12B). The resulting images confirm the channel diameters, spacing, and the 3D extent of the network.

Example 6

Flow Inside the Channel Network

Figure 13:
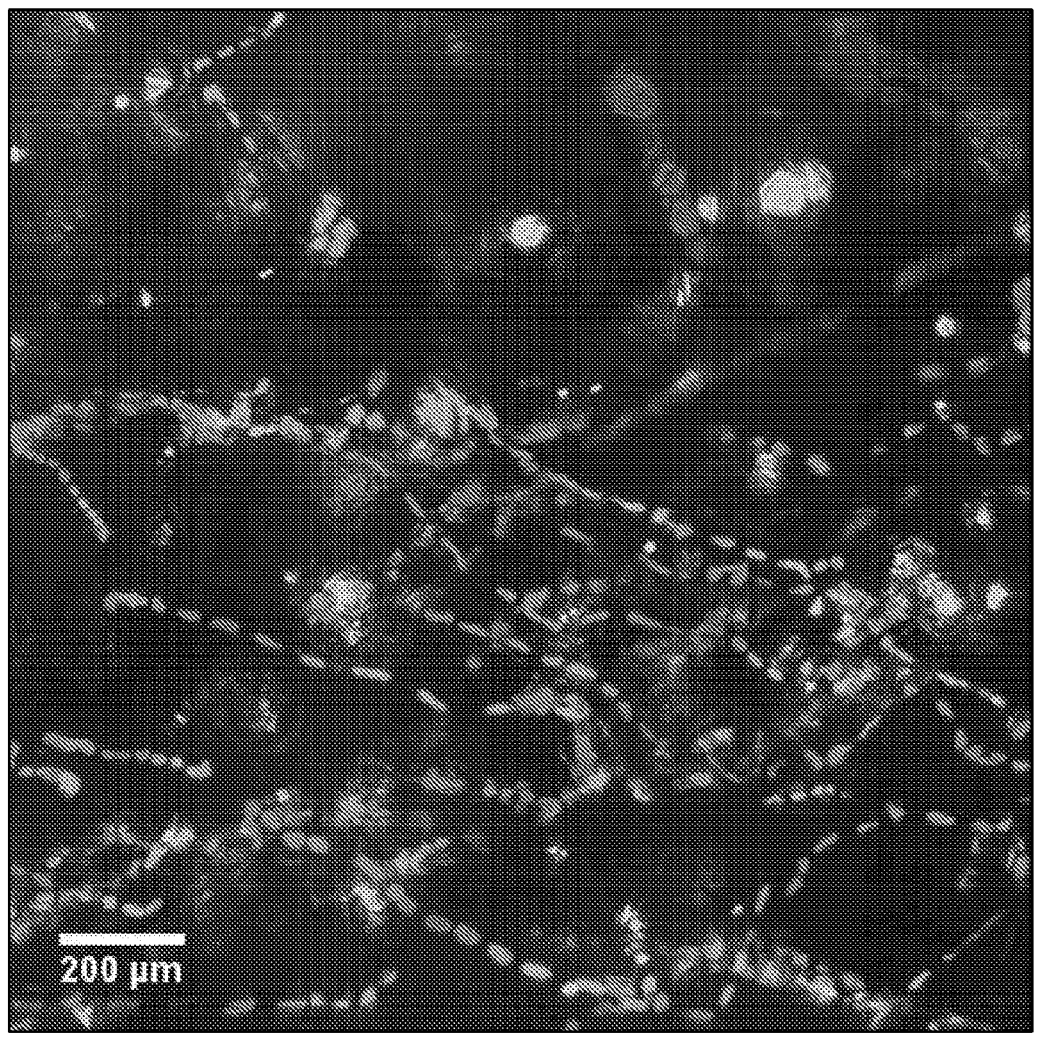
FIG. 13 shows a time lapse image constructed from video of fluorescent polystyrene particles flowing through a polydimethylsiloxane (PDMS) construct. Frames were taken from the video and assigned a color based on their time. In this image, the paths of the particles are shown by dotted paths.

Fluorescence microscopy is used to verify that the channel network is confluent and supports physiologically relevant flow. Images revealed the flow behavior of both fluorescent polystyrene spheres and fluorescently labeled blood. FIG. 13 shows a time-lapse image of the polystyrene particle flow from the video data produced using Image J. The solution used to image polystyrene particle flow consisted of stock 2 μm yellow-green Fluorspheres (Molecular Probes F8827) that had been diluted 10,000-fold. A syringe is connected to the device using 0.062"×0.014" FEP tubing (Upchurch) inserted into one of the two macrochannels. The solution is injected into a PDMS device at a flow rate of 25 μL/min using a syringe pump (Harvard Apparatus PHD 2000). The fluorescent particles are imaged using an inverted fluorescence microscope (Olympus IX70, EXFO X-cite 120 illuminator, Omega XF100-2 filter cube) using a Cascade 512b EMCCD camera (Roper Scientific) and homemade software written in Labview.

Example 7

Study of the Flow of Medium

Figure 14A:
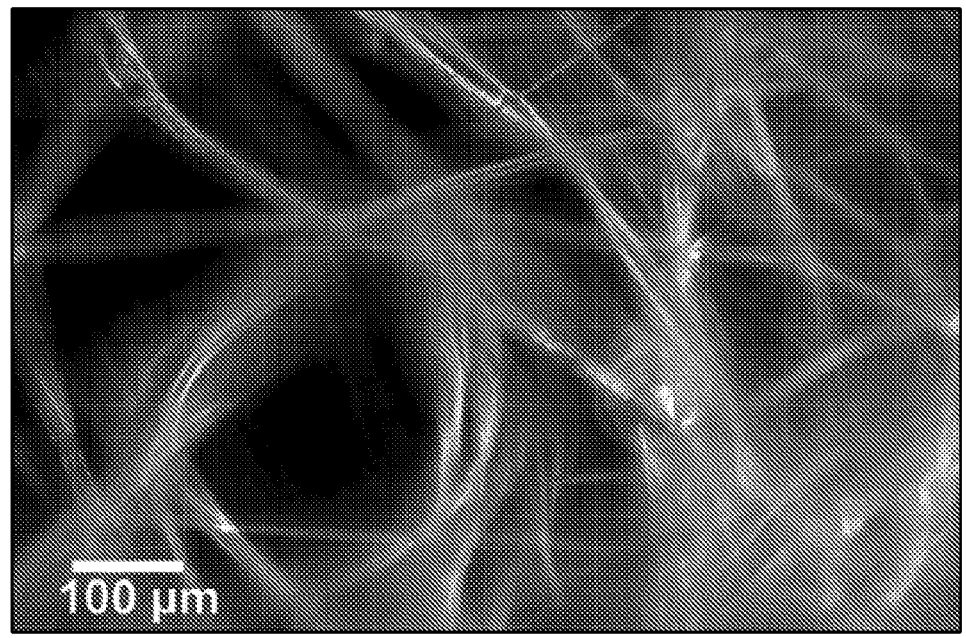
FIG. 14A-B show darkfield histology images of a sliced polydimethylsiloxane (PDMS) construct.
Figure 14B:
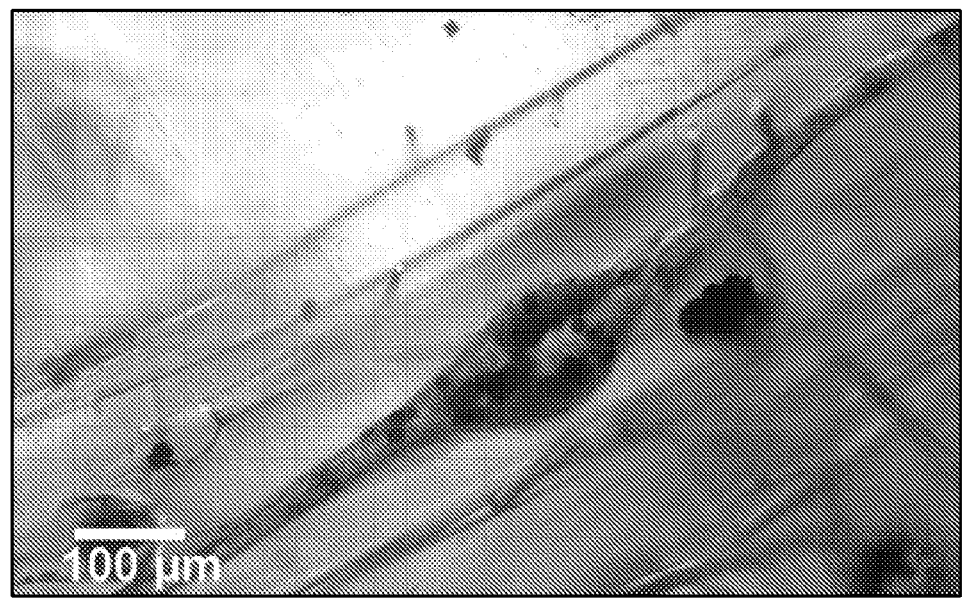

Heparinized (20 units/cc) whole rat blood is injected into a separate PDMS device to study the flow of a more physiologically relevant medium. The blood used for flow imaging is labeled with DiI (CellTracker CM-DiI C7001, Molecular Probes), put in a syringe tube, and connected to the device using tubing as before. Blood is introduced into the device at a flow rate of 25 μl/min for one hour using the syringe pump, and the labeled cells are imaged using the fluorescence microscope. The brightest particles account for approximately 1-2% of the total number of cells, according to comparisons of darkfield and fluorescence imaging of a droplet of labeled blood placed between two coverslips. As the blood fills the device, it exhibits a uniform red "blush". Under the applied flow rate, a pressure drop was measured (using an Omega PX26 transducer exposed to the flow via a tee inserted near the inlet) of approximately 50 mm Hg across the device; this pressure is within physiologic range. The velocity of the brighter entities in the blood flow was also calculated and found to be between tens to hundreds of microns per second, similar to the lower range of such velocities measured in vivo (Snicker et al., *Microvascular Research* 52:188-192 (1996), which is hereby incorporated by reference in its entirety). These data suggest that the microchannels formed using sacrificial microfibers share similar flow characteristics with natural microvascular systems and are compatible with the hemodynamic conditions present in normal human microvascular beds. The device is then fixed with formalin, manually sectioned, and imaged using darkfield microscopy (Nikon E800 upright microscope and QImaging Retiga Ex digital camera), demonstrating that erythrocytes are dispersed throughout the microchannel network (FIG. 14A-B).

Figure 15A:
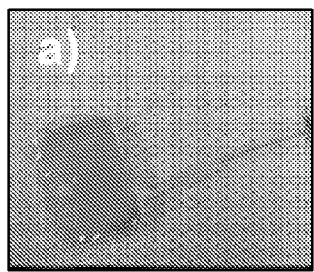
FIG. 15A-E show examples of vascular networks formed from a variety of materials. Figures A-D show a vascular network preform made from epoxy.
Figure 15B:
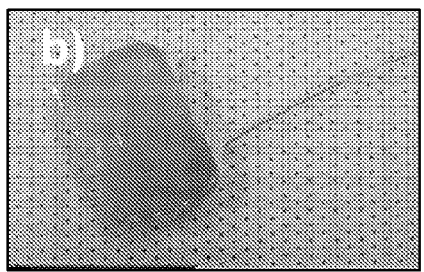
Figure 15C:
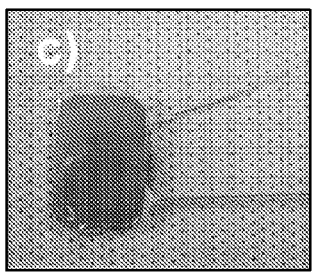
Figure 15D:
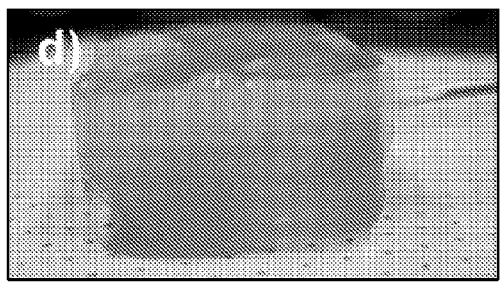
Figure 15E:
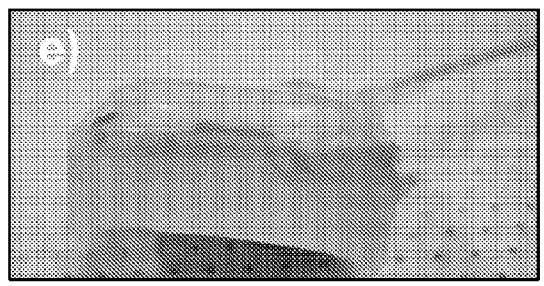

Various materials were tested for making the vascular network preform of the present invention and tested for the flow of medium. FIGS. 15A-D show various views of VNP made from epoxy. FIG. 15 A-C show sequential images obtained after flowing medium through the vascular network preform. The progressive color change is visible upon introduction of medium into the VNP. FIG. 15E is VNP made from polycaprolactone (PCL).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of producing a vascular network preform, said method comprising:
   forming a network of elongate fibers randomly extending in a non-repeating pattern from a sacrificial material;
   forming at least one elongate structure from a sacrificial material, wherein the elongate structure has a diameter greater than that of the elongate fibers;
   placing the network of elongate fibers and the at least one elongate structure in contact with one another following or during said forming a network of elongate fibers or said forming at least one elongate structure;
   applying a matrix around the network of elongate fibers in contact with the at least one elongate structure; and
   sacrificing the network of elongate fibers and the at least one elongate structure within the matrix to form a preform containing a vascular network of fine diameter tubes in fluid communication with at least one elongate passage having a diameter greater than that of the fine diameter tubes.

2. The method of claim 1, wherein said forming at least one elongate structure comprises forming at least two elongate structures, whereby said method produces a preform containing a vascular network of fine diameter tubes in contact with at least two elongate passages.

3. The method of claim 1, wherein the at least one elongate structure is branched.

4. The method of claim 1 wherein the elongate fibers are enmeshed with one another.

5. The method of claim 1, wherein the diameter of the elongate fibers is 1 to 100 microns.

6. The method of claim 1, wherein the diameter of the at least one elongate structure is 500 microns or greater.

7. The method of claim 1, wherein said forming a network of elongate fibers is carried out by melt-spinning, wet-spinning, dry-spinning, dry-jet wet spinning, electrospinning, or extrusion.

8. The method of claim 1, wherein the sacrificial material is selected from the group consisting of sucrose, polyethylene oxide, polyvinyl acetate, nylon, cellulose, polymethyl methacrylate, and other polymers.

9. The method of claim 1, wherein said sacrificing is carried out by solubilizing in a solvent, heat decomposition, reactive gas decomposition, light decomposition, enzymatic degradation, and/or catalytic degradation.

10. The method of claim 1, wherein the sacrificial materials used to form the network of elongate fibers and the at least one elongate structure are the same.

11. The method of claim 1, wherein the sacrificial materials used to form the network of elongate fibers and the at least one elongate structure are different.

12. The method of claim 1, wherein the matrix is a polymer.

13. The method of claim 12, wherein the polymer is selected from the group consisting of polydimethylsiloxane, polyglycerol sebacate, polycaprolactone, polylactic acid, polyglycolic acid, cellulose, alginate, agar, agarose, collagen I, collagen IV, hyaluronic acid, fibrin, poly-L-lactide, and poly(lactic-co-glycolic acid).

14. The method of claim 1 further comprising:
orienting the network of elongate fibers and the at least one elongate structure after said placing them in contact with one another.

15. The method of claim 1 further comprising:
connecting the network of elongate fibers and the at least one elongate structure, which are in contact with another, together.

16. The method of claim 1, wherein said applying a matrix comprises:
applying a flowable material around the network of elongate fibers in contact with the at least one elongate structure and
solidifying the flowable material to form a solid matrix.

17. The method of claim 16 further comprising:
adding a porogen to the matrix before or after said solidifying under conditions effective to introduce pores into the preform.

18. The method of claim 1 further comprising:
incorporating one or more drugs and/or biochemical agents into the matrix.

19. The method according to claim 18, wherein the drug or biochemical agent is selected from the group consisting of nutrients, growth factors, inducers of differentiation or de-differentiation, products of secretion, immunomodulators, inhibitors of inflammation, regression factors, and biological factors which enhance or allow ingrowth of the vascular, muscular, lymphatic or neural tissue.

20. The method of claim 1 further comprising:
seeding the preform containing a vascular network of fine diameter tubes in contact with at least one elongate passage with cells and
incubating the cells seeded in the preform.

21. The method of claim 20, wherein the cells are endothelial cells.

22. A solid preform comprising:
a solid matrix;
a vascular network of fine diameter tubes randomly extending in a non-repeating pattern within the solid matrix; and
at least one elongate passage having a diameter greater than that of the fine diameter tubes, said at least one elongate passage extending within the solid matrix and in fluid communication with the vascular network of fine diameter tubes.

23. The solid preform of claim 22, wherein the fine diameter tubes are enmeshed.

24. The solid preform of claim 22, wherein the at least one elongate passage is branched.

25. The solid preform of claim 22, wherein the diameter of the fine diameter tubes is 1 to 100 microns.

26. The solid preform of claim 22, wherein the diameter of the at least one elongate passage is 500 microns or greater.

27. The solid preform of claim 22, wherein the solid matrix is a polymer.

28. The solid preform of claim 27, wherein the polymer is selected from the group consisting of polydimethylsiloxane, polyglycerol sebacate, polycaprolactone, polylactic acid, polyglycolic acid, cellulose, alginate, agar, agarose, collagen I, collagen IV, hyaluronic acid, fibrin, poly-L-lactide, and poly(lactic-co-glycolic acid).

29. The solid preform of claim 22 further comprising:
a polymerization catalyst in the solid preform suitable to convert a healing agent to a filler at sites of injury or cracking in the solid preform.

30. The solid preform of claim 29, wherein the healing agent is located in the vascular network within the solid preform.

31. The solid preform of claim 22, wherein the solid preform is configured such that there is transfer of heat between the solid matrix and a fluid present in the vascular network.

32. The solid preform of claim 22, wherein the solid matrix is sealed so that fluids can only enter the solid preform through the at least one elongate passage.

33. The solid preform of claim 22, wherein the solid preform is porous.

34. The solid preform of claim 22, wherein said solid preform comprises at least two elongate passages, with at least one of the elongate passages being configured to permit entry of fluid in said vascular network and at least one of the elongate passages being configured to permit fluid to be withdrawn from said vascular network.

35. A cell seeded monolith comprising:
the solid preform of claim 22 and
cells seeded in the solid preform.

36. The cell seeded monolith of claim 35, wherein the cells are endothelial cells.

37. The cell seeded monolith of claim 35, wherein the monolith comprises one or more drugs and/or biochemical agents.

38. The cell seeded monolith of claim 37, wherein the drug or biochemical agent is selected from the group consisting of nutrients, growth factors, inducers of differentiation or de-differentiation, products of secretion, immunomodulators, inhibitors of inflammation, regression factors, and biological factors which enhance or allow ingrowth of the vascular, muscular, lymphatic or neural tissue.

39. A method of treating a patient for a condition requiring vascularization, said method comprising:
providing a cell seeded monolith according to claim 35;
selecting a subject with a condition requiring vascularization; and
implanting the cell seeded monolith into the selected subject.

40. The method of claim 39, wherein said condition is selected from the group consisting of wound healing, organ transplantation, tissue transplantation, and burn treatment.

41. A method of forming a self healing material system, said comprising:
providing the solid preform of claim 30;
allowing for release of the healing agent from the vascular network upon injury to or cracking of the solid preform, whereby the injury or crack is filled.

42. The method according to claim 41, wherein the healing agent is contained either in a plurality of microcapsules dispersed in the solid matrix or flows within the vascular network.

43. A method of transferring heat to a surface or volume comprising:
providing the solid preform of claim 31 and
passing a fluid through the vascular network whereby the solid preform heats or cools the fluid or the fluid heats or cools the solid preform.

44. A method of carrying out a biological reaction comprising:
providing the cell seeded monolith of claim 35 and
passing a fluid through the vascular network under conditions effective to carry out the biological reaction.

45. The method according to claim 44, wherein the biological reaction produces a biochemical agent or molecule.

46. The method according to claim 44, where the biological reaction is an assay to determine the effect of a drug or biochemical agent on the cells seeded within the monolith.

47. The method according to claim 44, wherein the fluid comprises cells or cellular materials.

* * * * *

UNITED STATES PATENT AND TRADEMARK OFFICE
CERTIFICATE OF CORRECTION

PATENT NO. : 9,242,027 B2
APPLICATION NO. : 13/054450
DATED : January 26, 2016
INVENTOR(S) : Leon M. Bellan, Harold Craighead and Jason A. Spector Page 1 of 1

It is certified that error appears in the above-identified patent and that said Letters Patent is hereby corrected as shown below:

In claim 41, col. 24, line 46, delete "said comprising" and insert in its place "said method comprising".

Signed and Sealed this
Thirty-first Day of May, 2016

Michelle K. Lee
*Director of the United States Patent and Trademark Office*